(12) United States Patent
Bannigan et al.

(10) Patent No.: US 9,198,696 B1
(45) Date of Patent: Dec. 1, 2015

(54) CROSS-CONNECTOR AND RELATED METHODS

(75) Inventors: Shaeffer Bannigan, Carlsbad, CA (US); Michael Brotman, San Diego, CA (US); Tara Stevenson, La Jolla, CA (US)

(73) Assignee: NuVasive, Inc., San Diego (*) Notice: Subject to any disclaimer, the term of this patent is extended or adjusted under 35 U.S.C. 154(b) by 174 days.

(21) Appl. No.: 13/118,323

(22) Filed: May 27, 2011

Related U.S. Application Data

(60) Provisional application No. 61/348,821, filed on May 27, 2010.

(51) Int. Cl.
*A61B 17/70* (2006.01)

(52) U.S. Cl.
CPC ......... *A61B 17/7052* (2013.01); *A61B 17/7023* (2013.01); *A61B 17/7025* (2013.01); *A61B 17/7049* (2013.01)

(58) Field of Classification Search
CPC ........... A61B 17/7049; A61B 17/7052; A61B 17/705; A61B 17/7023; A61B 17/7025
USPC .................................................. 606/250–253
See application file for complete search history.

(56) References Cited

U.S. PATENT DOCUMENTS

| | | |
|---|---|---|
| 4,361,141 A | 11/1982 | Tanner |
| 4,569,338 A | 2/1986 | Edwards |
| 4,641,636 A | 2/1987 | Cotrel |
| 4,771,767 A | 9/1988 | Steffee |
| 4,805,602 A | 2/1989 | Puno et al. |
| 4,946,458 A | 8/1990 | Harms et al. |
| 4,998,936 A | 3/1991 | Mehdian |
| 5,005,562 A | 4/1991 | Cotrel |
| 5,034,011 A | 7/1991 | Howland |
| 5,042,982 A | 8/1991 | Harms et al. |
| 5,084,049 A | 1/1992 | Asher et al. |

(Continued)

FOREIGN PATENT DOCUMENTS

| | | |
|---|---|---|
| BR | PI0801130 | 6/2011 |
| DE | 3841008 | 6/1990 |

(Continued)

OTHER PUBLICATIONS

Beadling, "Harrington put the steel in spinal fixation", *Orthopedics Today*, (Jun. 2000), 6 pgs.

(Continued)

*Primary Examiner* — Eduardo C Robert
*Assistant Examiner* — Julianna N Harvey
(74) *Attorney, Agent, or Firm* — Jonathan Spangler; Jennifer Russell

(57) ABSTRACT

A cross-connector, sized and dimensioned to stabilize the distance between a pair of rods in the spine. The cross-connector includes a first coupling assembly, a second coupling assembly, and a connecting device, extending therebetween. Each coupling assembly further includes a coupler, which attaches to a tulip head, and a camming assembly. The connecting device further includes a first arm element, a second arm element, and a screw. The arm elements move within the ball joints of the couplers and pivot around the screw, allowing a surgeon to adjust the length of the cross-connector and place the cross-connector above and around features within the body. The camming assemblies lock the tulip heads and the arm elements in place on the couplers. The screw locks the center rotation of the cross-connector.

5 Claims, 22 Drawing Sheets

(56) References Cited

U.S. PATENT DOCUMENTS

| | | |
|---|---|---|
| 5,092,866 A | 3/1992 | Breard et al. |
| 5,092,867 A | 3/1992 | Harms et al. |
| 5,092,893 A | 3/1992 | Smith |
| 5,129,388 A | 7/1992 | Vignaud et al. |
| 5,154,718 A | 10/1992 | Cozad et al. |
| 5,176,680 A | 1/1993 | Vignaud et al. |
| 5,196,013 A | 3/1993 | Harms et al. |
| 5,207,678 A | 5/1993 | Harms et al. |
| 5,234,431 A | 8/1993 | Keller |
| 5,261,907 A | 11/1993 | Vagnaud et al. |
| 5,275,600 A | 1/1994 | Allard et al. |
| 5,312,405 A | 5/1994 | Korotko et al. |
| 5,330,473 A | 7/1994 | Howland |
| 5,375,823 A | 12/1994 | Navas |
| 5,387,213 A | 2/1995 | Breard et al. |
| 5,397,363 A | 3/1995 | Gelbard |
| 5,403,314 A | 4/1995 | Currier |
| 5,466,237 A | 11/1995 | Byrd, III et al. |
| 5,474,555 A | 12/1995 | Puno et al. |
| 5,478,340 A | 12/1995 | Kluger |
| 5,480,401 A | 1/1996 | Navas |
| 5,498,263 A | 3/1996 | Dinello et al. |
| 5,501,684 A | 3/1996 | Schlapfer et al. |
| 5,505,731 A | 4/1996 | Tornier |
| 5,522,816 A | 6/1996 | Dinello et al. |
| 5,536,268 A | 7/1996 | Griss |
| 5,540,688 A | 7/1996 | Navas |
| 5,545,163 A | 8/1996 | Miller et al. |
| 5,545,166 A | 8/1996 | Howland |
| 5,562,661 A | 10/1996 | Yoshimi et al. |
| 5,569,246 A | 10/1996 | Ojima et al. |
| 5,601,554 A | 2/1997 | Howland et al. |
| 5,607,425 A | 3/1997 | Rogozinski |
| 5,624,442 A | 4/1997 | Mellinger et al. |
| 5,630,816 A | 5/1997 | Kambin |
| 5,643,264 A | 7/1997 | Sherman et al. |
| 5,645,544 A | 7/1997 | Tai et al. |
| 5,665,122 A | 9/1997 | Kambin |
| 5,667,508 A | 9/1997 | Errico et al. |
| 5,669,910 A | 9/1997 | Korhonen et al. |
| 5,669,911 A | 9/1997 | Errico et al. |
| 5,672,176 A | 9/1997 | Biedermann et al. |
| 5,676,665 A | 10/1997 | Bryan |
| 5,676,703 A | 10/1997 | Gelbard |
| 5,681,311 A | 10/1997 | Foley et al. |
| 5,688,272 A | 11/1997 | Montague et al. |
| 5,690,630 A | 11/1997 | Errico et al. |
| 5,693,053 A | 12/1997 | Estes |
| 5,702,393 A | 12/1997 | Pfaifer |
| 5,704,936 A | 1/1998 | Mazel |
| 5,716,355 A | 2/1998 | Jackson et al. |
| 5,725,527 A | 3/1998 | Biedermann et al. |
| 5,735,852 A | 4/1998 | Amrein et al. |
| 5,776,135 A | 7/1998 | Errico et al. |
| 5,800,435 A | 9/1998 | Errico et al. |
| 5,863,293 A | 1/1999 | Richelsoph |
| 5,873,878 A | 2/1999 | Harms et al. |
| 5,928,232 A | 7/1999 | Howland et al. |
| 5,928,237 A | 7/1999 | Farris et al. |
| 5,938,663 A | 8/1999 | Petreto |
| 5,944,719 A | 8/1999 | Leban |
| 5,944,720 A | 8/1999 | Lipton |
| 5,947,966 A | 9/1999 | Drewry et al. |
| 5,951,555 A | 9/1999 | Rehak et al. |
| 5,954,722 A | 9/1999 | Bono |
| 5,954,725 A | 9/1999 | Sherman et al. |
| 5,961,516 A | 10/1999 | Graf |
| 5,980,521 A | 11/1999 | Montague et al. |
| 5,980,523 A | 11/1999 | Jackson et al. |
| 6,004,322 A | 12/1999 | Bernstein |
| 6,030,389 A | 2/2000 | Wagner et al. |
| 6,063,089 A | 5/2000 | Errico et al. |
| 6,074,391 A | 6/2000 | Metz-Stavenhagen |
| 6,083,226 A | 7/2000 | Fiz |
| 6,113,600 A | 9/2000 | Drummond et al. |
| 6,136,003 A | 10/2000 | Hoeck et al. |
| 6,139,548 A | 10/2000 | Errico |
| 6,171,311 B1 | 1/2001 | Richelsoph |
| 6,179,838 B1 | 1/2001 | Fiz |
| 6,187,005 B1 | 2/2001 | Brace et al. |
| 6,190,388 B1 | 2/2001 | Michelson |
| 6,217,578 B1 | 4/2001 | Crozet et al. |
| 6,224,598 B1 | 5/2001 | Jackson |
| 6,234,705 B1 | 5/2001 | Troxell |
| 6,238,396 B1 | 5/2001 | Lombardo |
| 6,241,730 B1 | 6/2001 | Alby |
| 6,264,658 B1 | 7/2001 | Lee et al. |
| 6,267,765 B1 | 7/2001 | Taylor et al. |
| 6,273,914 B1 | 8/2001 | Papas |
| 6,280,445 B1 | 8/2001 | Morrison et al. |
| 6,283,967 B1 | 9/2001 | Troxell et al. |
| 6,296,644 B1 | 10/2001 | Saurat et al. |
| 6,306,137 B2 | 10/2001 | Troxell |
| 6,325,802 B1 | 12/2001 | Frigg |
| 6,328,740 B1 | 12/2001 | Richelsoph |
| 6,328,741 B1 | 12/2001 | Richelsoph |
| 6,379,354 B1 | 4/2002 | Rogozinski |
| 6,402,751 B1 | 6/2002 | Hoeck et al. |
| 6,413,258 B1 | 7/2002 | Bernhardt, Jr. |
| 6,482,207 B1 | 11/2002 | Errico |
| 6,485,491 B1 | 11/2002 | Farris et al. |
| 6,524,310 B1 | 2/2003 | Lombardo et al. |
| 6,554,832 B2 | 4/2003 | Shluzas |
| 6,602,253 B2 | 8/2003 | Richelsoph et al. |
| 6,616,668 B2 | 9/2003 | Altarac et al. |
| 6,626,904 B1 | 9/2003 | Jammet et al. |
| 6,641,583 B2 | 11/2003 | Shluzas et al. |
| 6,736,817 B2 | 5/2004 | Troxell et al. |
| 6,752,807 B2 | 6/2004 | Lin et al. |
| 6,761,721 B2 | 7/2004 | Burgess et al. |
| 6,783,526 B1 | 8/2004 | Lin et al. |
| 6,872,208 B1 | 3/2005 | McBride et al. |
| 6,875,211 B2 | 4/2005 | Nichols et al. |
| 6,887,241 B1 | 5/2005 | McBride et al. |
| 6,899,714 B2 | 5/2005 | Vaughan |
| 6,958,066 B2 | 10/2005 | Richelsoph et al. |
| 6,960,212 B2 | 11/2005 | Richelsoph et al. |
| 7,029,474 B2 | 4/2006 | Richelsoph et al. |
| 7,066,938 B2 | 6/2006 | Slivka et al. |
| 7,083,622 B2 | 8/2006 | Simonson |
| 7,104,993 B2 | 9/2006 | Baynham et al. |
| 7,122,036 B2 | 10/2006 | Vanacker |
| 7,137,986 B2 | 11/2006 | Troxell et al. |
| 7,160,301 B2 | 1/2007 | Cordaro |
| 7,406,775 B2 | 8/2008 | Funk et al. |
| 7,678,112 B2 | 3/2010 | Rezach |
| 8,062,339 B2 | 11/2011 | Hammer et al. |
| 2001/0034521 A1 | 10/2001 | Bailey et al. |
| 2002/0052603 A1 | 5/2002 | Nichols et al. |
| 2002/0143330 A1 | 10/2002 | Shluzas |
| 2002/0169448 A1 | 11/2002 | Vanacker |
| 2003/0023244 A1 | 1/2003 | Richelsoph et al. |
| 2003/0028191 A1 | 2/2003 | Shluzas |
| 2003/0045878 A1 | 3/2003 | Petit et al. |
| 2003/0060823 A1 | 3/2003 | Bryan |
| 2003/0149432 A1 | 8/2003 | Frigg et al. |
| 2003/0153917 A1 | 8/2003 | Richelsoph et al. |
| 2003/0163133 A1 | 8/2003 | Altarac et al. |
| 2003/0212398 A1 | 11/2003 | Jackson |
| 2004/0116928 A1 | 6/2004 | Young et al. |
| 2004/0138662 A1 | 7/2004 | Landry et al. |
| 2004/0147928 A1 | 7/2004 | Landry et al. |
| 2004/0260287 A1 | 12/2004 | Ferree |
| 2005/0010217 A1 | 1/2005 | Dalton |
| 2005/0070901 A1 | 3/2005 | David |
| 2005/0080416 A1 | 4/2005 | Ryan et al. |
| 2005/0090821 A1 | 4/2005 | Berrevoets et al. |
| 2005/0192572 A1 | 9/2005 | Abdelgany et al. |
| 2005/0228326 A1 | 10/2005 | Kalfas et al. |
| 2005/0228382 A1 | 10/2005 | Richelsoph et al. |
| 2005/0277923 A1 | 12/2005 | Sweeney |
| 2005/0288670 A1 | 12/2005 | Panjabi et al. |
| 2006/0036252 A1 | 2/2006 | Baynham et al. |
| 2006/0052783 A1 | 3/2006 | Dant et al. |

(56) References Cited

U.S. PATENT DOCUMENTS

| | | |
|---|---|---|
| 2006/0052786 A1 | 3/2006 | Dant et al. |
| 2006/0058789 A1 | 3/2006 | Kim et al. |
| 2006/0064091 A1 | 3/2006 | Ludwig et al. |
| 2006/0064093 A1 | 3/2006 | Thramann et al. |
| 2006/0149229 A1 | 7/2006 | Kwak et al. |
| 2006/0217718 A1 | 9/2006 | Chervitz et al. |
| 2006/0229606 A1 | 10/2006 | Clement et al. |
| 2006/0235393 A1 | 10/2006 | Bono et al. |
| 2006/0247624 A1 | 11/2006 | Banouskou et al. |
| 2006/0264933 A1 | 11/2006 | Baker et al. |
| 2006/0271045 A1 | 11/2006 | Hubbard et al. |
| 2006/0282074 A1 | 12/2006 | Renaud et al. |
| 2006/0282075 A1 | 12/2006 | Labrom et al. |
| 2006/0282076 A1 | 12/2006 | Labrom et al. |
| 2006/0282077 A1 | 12/2006 | Labrom et al. |
| 2006/0282078 A1 | 12/2006 | Labrom et al. |
| 2006/0282079 A1 | 12/2006 | Labrom et al. |
| 2007/0049932 A1 | 3/2007 | Richelsoph et al. |
| 2007/0055239 A1 | 3/2007 | Sweeney et al. |
| 2007/0083201 A1 | 4/2007 | Jones et al. |
| 2007/0149973 A1 | 6/2007 | Clement et al. |
| 2007/0173829 A1 | 7/2007 | Drewry et al. |
| 2007/0173833 A1 | 7/2007 | Butler et al. |
| 2007/0213721 A1 | 9/2007 | Markworth et al. |
| 2007/0213723 A1 | 9/2007 | Markworth et al. |
| 2007/0233062 A1 | 10/2007 | Berry |
| 2007/0233090 A1 | 10/2007 | Naifeh |
| 2007/0233119 A1 | 10/2007 | Markworth |
| 2007/0270808 A1 | 11/2007 | Drewry et al. |
| 2007/0270809 A1 | 11/2007 | Drewry et al. |
| 2007/0288009 A1 | 12/2007 | Brown et al. |
| 2008/0021464 A1 | 1/2008 | Morin et al. |
| 2008/0051780 A1 | 2/2008 | Vaidya et al. |
| 2008/0071273 A1 | 3/2008 | Hawkes et al. |
| 2008/0091204 A1 | 4/2008 | Kuiper et al. |
| 2008/0109039 A1 | 5/2008 | Michielli et al. |
| 2008/0140075 A1 | 6/2008 | Ensign et al. |
| 2008/0172093 A1 | 7/2008 | Nilsson |
| 2008/0177315 A1* | 7/2008 | Usher ............................ 606/253 |
| 2008/0177323 A1 | 7/2008 | Null et al. |
| 2008/0255617 A1 | 10/2008 | Cho et al. |
| 2008/0269742 A1 | 10/2008 | Levy et al. |
| 2008/0306534 A1 | 12/2008 | Winslow et al. |
| 2008/0306535 A1 | 12/2008 | Winslow et al. |
| 2008/0312692 A1 | 12/2008 | Brennan et al. |
| 2009/0018586 A1* | 1/2009 | Butler et al. .................. 606/278 |
| 2009/0043338 A1 | 2/2009 | Laager et al. |
| 2009/0062860 A1 | 3/2009 | Frasier et al. |
| 2009/0125065 A1 | 5/2009 | Laager et al. |
| 2009/0216277 A1 | 8/2009 | Tornier et al. |
| 2009/0318968 A1 | 12/2009 | Duggal et al. |
| 2010/0094345 A1 | 4/2010 | Saidha et al. |
| 2010/0094346 A1 | 4/2010 | Matityahu |
| 2010/0094349 A1 | 4/2010 | Hammer et al. |
| 2010/0160981 A1 | 6/2010 | Butler et al. |
| 2010/0191289 A1 | 7/2010 | Ludwig et al. |
| 2010/0198260 A1 | 8/2010 | Gabelberger et al. |
| 2010/0204733 A1 | 8/2010 | Rathbun et al. |
| 2010/0211100 A1 | 8/2010 | Mack |
| 2010/0268279 A1 | 10/2010 | Gabelberger et al. |
| 2010/0274286 A1* | 10/2010 | Blain et al. ..................... 606/250 |
| 2010/0324599 A1 | 12/2010 | Montello et al. |
| 2011/0034957 A1 | 2/2011 | Biedermann |
| 2011/0046675 A1* | 2/2011 | Barrus et al. .................. 606/252 |
| 2011/0071569 A1 | 3/2011 | Black |
| 2011/0106178 A1 | 5/2011 | Schwab |
| 2011/0184462 A1 | 7/2011 | Gil et al. |
| 2012/0029566 A1 | 2/2012 | Rezach |
| 2012/0071926 A1 | 3/2012 | Jani et al. |
| 2012/0101529 A1 | 4/2012 | Ludwig et al. |
| 2012/0130436 A1 | 5/2012 | Haskins et al. |

FOREIGN PATENT DOCUMENTS

| | | |
|---|---|---|
| DE | 9004960.8 | 8/1992 |
| EP | 0283373 | 9/1988 |
| EP | 1743585 | 1/2007 |
| FR | 2624720 | 6/1989 |
| WO | WO 95/13754 | 5/1995 |
| WO | WO 2006/025919 | 3/2006 |
| WO | WO 2007/130007 | 11/2007 |
| WO | WO 2010/045219 | 4/2010 |
| WO | WO 2011/057178 | 5/2011 |

OTHER PUBLICATIONS

Dipreta, "The Iliac Nail/Screw in a Modified Galveston Technique for Sacropelvic Fixation", *Am. Acad. of Ortho. Surg.*, 67$^{th}$ mtg., PE184, (Mar. 19, 2000), 1 pg.

Ebrahim, "Posterior Lateral Mass Screw Fixation: Anatomic and Radiographic Considerations", *U.P.O.J.* vol. 12 (Spring 1999), 66-72.

Erickson, "Biomechanical Assessment of Conventional Unit Rod Fixation Versus a Unit Rod Pedicle Screw Construct", *Spine*, vol. 29, No. 12, (2004), 1314-1319.

Pham, "Upper cervical spine surgery in rheumatoid arthritis: retrospective study of 30 patients followed for two years or more after Cotrel-Dubousset instrumentation", *Joint Bone Spine*, 67 (2000), 434-440.

Sanders, "Treating, managing spinal deformity in young patients", Orthopedics Today (Jul. 2001), 12 pgs.

Spiegel, "Anterior instrumentation in the Treatment of Scolisosis" *U.P.O.J.*, vol. 11, (Spring 1998), 19-26.

Wood, "Torsional Rigidity of Scoliosis Constructs", *Spine*, vol. 25, No. 15, (2000), 1893-1898.

* cited by examiner

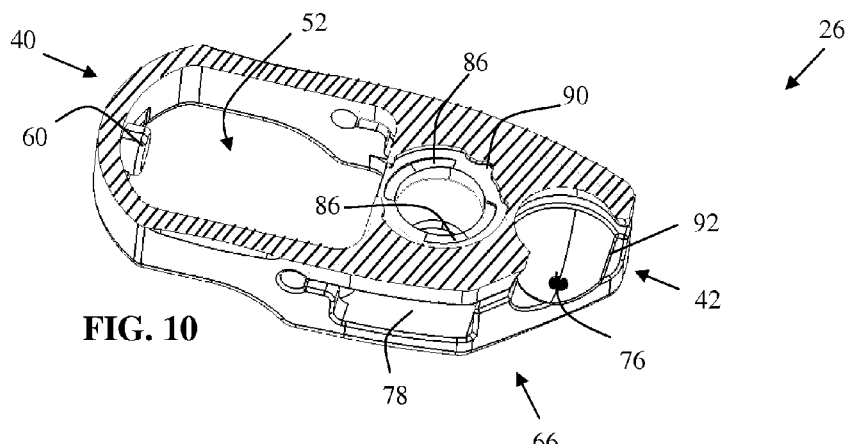
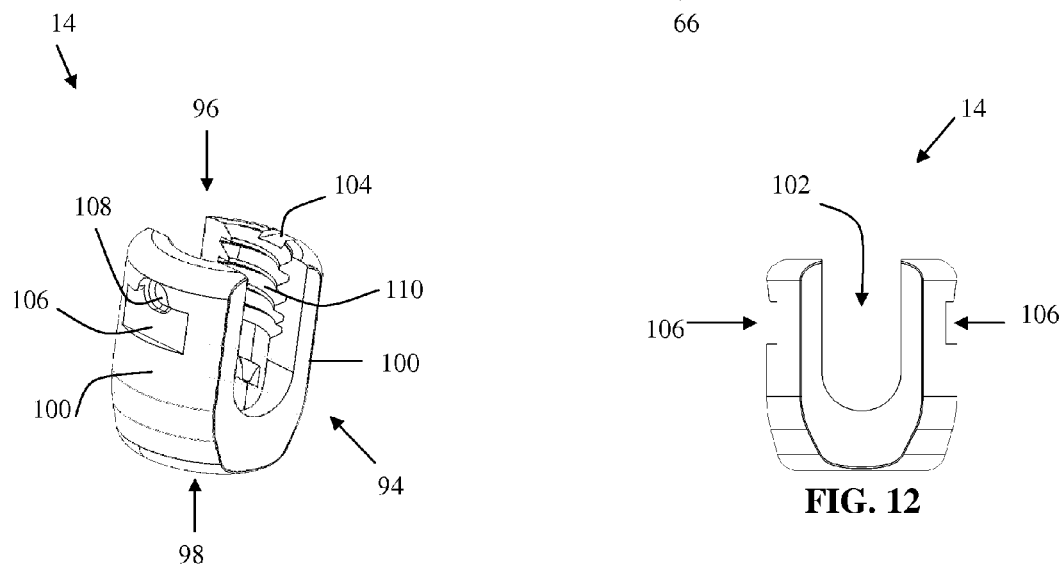
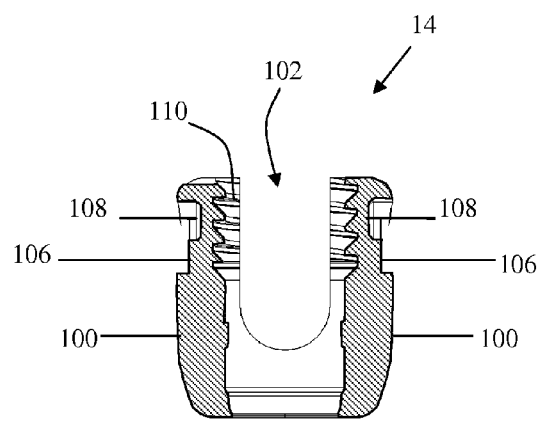

CROSS-CONNECTOR AND RELATED METHODS

CROSS-REFERENCE TO RELATED APPLICATIONS

This application is a non-provisional patent application and claims the benefit of priority from commonly owned U.S. Provisional Patent Application Ser. No. 61/348,821, entitled "Cross-Connector and Related Methods," filed on May 27, 2010, the entire contents of which are each hereby expressly incorporated by reference into this disclosure as if set forth in its entirety herein.

FIELD

The present application describes cross-connectors used to link bilateral spinal fixation constructs.

BACKGROUND

The spinal column is a highly complex system of bones and connective tissues that provide support for the body and protect the delicate spinal cord and nerves. The spinal column includes a series of vertebral bodies stacked one atop the other, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord is located behind the vertebral bodies.

There are many types of spinal column disorders including scoliosis (abnormal lateral curvature of the spine), excess kyphosis (abnormal forward curvature of the spine), excess lordosis (abnormal backward curvature of the spine), spondylothesis (forward displacement of one vertebra over another), and other disorders caused by abnormalities, disease or trauma, such as ruptured or slipped discs, degenerative disc disease, fractured vertebra and the like. Patients that suffer from such conditions usually experience extreme and debilitating pain, as well as diminished nerve function.

To correct these spinal column disorders, a pair of rods is usually implanted into the spine using pedicle screw systems on the vertebral bodies. Cross-connectors that attach directly to spinal rods provide added rigidity to the spinal rod fixation constructs.

Currently, some cross-connectors come in fixed configurations which limit a surgeon's ability to determine the optimal spacing between a pair of spinal rods. Other cross-connectors are adjustable to adjust overall length, however they are only moveable in the lateral direction, which prevents the surgeon from placing the cross-connector in any area of a patient's body where anatomical features would impede the movement of the cross-connector.

Therefore, a need exists for improved cross-connectors.

SUMMARY

The present invention solves the above-identified drawbacks with the prior art by providing a cross-connector with an adjustable length that can be placed above and around any spinous processes.

The cross-connector includes a first coupling assembly, a second coupling assembly, and a connecting device extending therebetween. The first coupling assembly attaches to a first tulip head on a first pedicle screw, the second coupling assembly attaches to a second tulip head on a second pedicle screw, and the connecting device allows a surgeon to adjust the overall length of the cross-connector.

The first coupling assembly has nearly identical (e.g. mirror image) features and functions as the second coupling assembly. Each coupling assembly includes a coupler and a camming assembly. The connecting device includes a first arm element, a second arm element, and a screw, connecting both arm elements together.

The terms distal and proximal are relative to the screw in the connecting device. Distal refers to a location away from the screw, and proximal is an area closer to the screw.

The coupler is a polygon shaped body, having a distal end and a proximal end. The body further includes a first body section at the distal end and a second body section at the proximal end. A cut-out is in the wall between the first body section and the second body section for stability purposes.

The first body section of the coupler includes a side wall at the distal end and an aperture, having a first edge and a second edge. A surface extends proximally from the side wall and terminates at the first edge of the aperture. The side wall is curved and dimensioned to match the walls of the tulip head, and includes a protrusion that extends proximally from the side wall. The protrusion has a cylindrical shape and is sized and dimensioned for being received within the cylindrical recess in the tulip head. The protrusion also provides the first connection area between the coupler and the tulip head. The flange in the cam in the camming assembly in the second body section provides the second connection area between the coupler and the tulip head. The aperture, the first edge, and the second edge are all sized and dimensioned for receiving the tulip head and the set screw of a pedicle screw.

The second body section of the coupler extends proximally from the second edge of the aperture in the first body section. The second body section includes a tip at the proximal end, a first surface, a second surface, and a side surface, extending between the first surface and the second surface. A space separates the first surface from the second surface. An aperture extends through the second body section from the first surface to the second surface. The first surface has a perimeter of the aperture. The second surface includes a recess surrounding the aperture. The side surface includes a spherical cut-out and a rectangular cut-out.

The tip at the proximal end of the coupler has a flat surface for visual purposes and will always face the tip of the second coupler in the same horizontal line.

The aperture includes a first shelf and second shelf. The first shelf is located approximately midway through the aperture between the first surface and the second surface, and extends around the circumference of the aperture. The first shelf includes two ramps positioned on opposite sides of the aperture from one another. The curvature of the ramps corresponds with the ramped surfaces on the pin in the camming assembly. The pin will "move up" one of the ramps as it is rotated clockwise approximately 115 degrees to become "locked." When the pin is "locked," the first and second surfaces clamp around the spherical body of the first arm element, and the flange of the cam presses against the rectangular recess in the tulip head.

The second shelf in the aperture is located about three quarters of the distance from the first surface to the second surface, and extends around the circumference of the aperture. This shelf supports the cam in the camming assembly when the pin rotates the cam. The aperture terminates within a recess that is sized and dimensioned for receiving the weld cap of the camming assembly on the second surface.

The perimeter of the aperture includes a first recess and second recess, both of which have semi-circular shapes. The first recess and the second recess correspond with the first protrusion and the second protrusion on the head of the pin of the camming assembly. The first recess has a larger diameter than the second recess, and guides the first protrusion as the pin moves up the ramp. As the pin finishes rotating 115 degrees or reaches the top of the ramp, the second protrusion of the pin becomes positioned within the second recess. This positioning will be the result of a snap fit engagement between the second protrusion and the second recess. Thus, the surgeon knows by feel that the pin is locked and that this rotation is complete.

The spherical cut-out in the side surface is sized and dimensioned to receive the spherical body at the distal end of the first arm element. This cut-out acts like a ball joint by providing the greatest degree of movement for the spherical body when the surgeon is adjusting the length of the connecting device. Additionally, the spherical cut-out is surrounded by smaller spherical cut-outs. Adjacent to the smaller spherical cut-outs is the rectangular cut-out. The smaller spherical cut-outs and the rectangular cut-out provide extra flexibility to the coupler when the first and second surfaces clamp to the spherical body of the first arm element.

The space between the first surface and second surface of the coupler also provides flexibility to the coupler when the spherical body of the arm element rotates within the spherical cut-out when the surgeon adjusts the length of the connecting device.

The first and second embodiments of the cross-connector connect to the tulip heads on pedicle screws. The tulip head includes a U shaped body, having a top and a bottom. The body is dimensioned for receiving a rod, and further includes walls and an aperture. One of the walls has a cut-out at the top for visual purposes to allow a surgeon to line up the set screw with the body of the tulip head. Both of the walls have a rectangular recess that provides an area where the cam presses against the tulip head, thereby locking the tulip head in place. Additionally, each wall has a cylindrical recess that corresponds with the cylindrical protrusion in the coupler. The aperture has a threaded region that is sized and dimensioned for receiving a set screw that connects a rod to the tulip head.

The camming assembly in the coupler includes a pin, a cam, and a weld cap. While the pin rotates the cam, the pin cannot move the weld cap which is welded to the pin.

The pin includes a top and a bottom, having a head, a middle section, and a stem, between the top and the bottom. The head includes a recess at the top, ramped surfaces at the bottom, and a first protrusion and a second protrusion, extending between the top and bottom of the head. The recess is sized and dimensioned for receiving a driver to rotate the pin and the cam. The ramped surfaces correspond with the curvature of the ramps in the coupler. By way of example only, the first protrusion and the second protrusion are generally semi-circular in shape and match the shape of the first recess and second recess respectively in the aperture of the coupler. The first protrusion has a larger diameter than the second protrusion.

The middle section of the pin includes a step that is never in direct contact with the shelf of the cam such that the cam has space to move around the stem. The stem is sized and dimensioned to fit within the aperture of the cam and the aperture of the weld cap.

The cam includes a curved body, having a flange. The curved body further includes a circular opening having an aperture and a shelf. While the opening is sized and dimensioned for receiving both the middle section and the stem of the pin, the aperture can generally accommodate only the stem. The diameter of the aperture is larger than the diameter of the stem to allow the cam to move easily around the stem. The flange is curved so that the cam can easily move along the curved walls of the tulip head before pressing against the rectangular recess in the tulip head, thereby providing the second area of contact between the coupler and the tulip head.

The weld cap is disk shaped and sized and dimensioned for fitting within the recess in the second surface of the coupler. The weld cap also includes an aperture that is sized and dimensioned to contain the stem of the pin.

The connecting device includes a first arm element, a second arm element, and a screw.

The first arm element includes an elongated member, having a spherical body at the distal end, and a disk shaped body at the proximal end. By way of example only, the elongated member makes an angle of 27 degrees with the horizontal. The spherical body rotates within the spherical cut-out of the coupler. The disk shaped body includes an aperture and a threaded region that are both sized and dimensioned for receiving the threaded shank of the screw.

Similar to the first arm element, the second arm element includes an elongated member, having a spherical body at the distal end, and a disk shaped body at the proximal end. An angled surface with a cut-out for stability extends between the elongated member and the disk shaped body. The elongated member makes an angle of 27 degrees with the horizontal. The spherical body is sized and dimensioned to rotate within the spherical cut-out of the coupler when the surgeon adjusts the length of the connecting device. The disk shaped body includes an aperture, extending therethrough. The aperture includes a shelf that extends around the circumference of the aperture. The aperture and the shelf are both sized and dimensioned for receiving the head of the screw in the connecting device. The angled surface extends the overall length of the second arm element such that the disk shaped body of the second arm element rests vertically above the disk shaped body of the first arm element, and the screw can lock both disk shaped bodies together.

The screw includes a head, having a recess and a threaded shank. The head is rounded and dimensioned to pass through the aperture in the second arm element. The recess is sized and dimensioned for receiving a driver which allows a surgeon to engage the threaded shank with the threaded region in the aperture of the first arm element. When the threaded shank is completely engaged with the threaded region of the aperture, the cross-connector will not be able to rotate in the center and the head of the screw will rest on the shelf of the aperture in the second arm element.

The screw acts as a center pivot point for the connecting device, where the first arm element and second arm element move back and forth to adjust the overall length of the cross-connector. In the preferred embodiment, this range of movement is limited to 20 degrees in both directions. This angular movement allows a surgeon to place the connecting device around any features within the body.

In use, the cross-connector is applied after the pedicle screws and rods have been fully implanted in the spine. The cross-connector is then installed over the tulip heads of the pedicle screws. More specifically, the surgeon inserts the cylindrical protrusion in the first coupler into the cylindrical recess of the first tulip head of a first pedicle screw, and repeats this process to connect the second coupler to a second tulip head on a second pedicle screw on the same vertebral body. At this point, the tip of the first coupler will be in the same horizontal line as the tip of the second coupler.

To determine the optimal length of the cross-connector, the surgeon pivots the first arm element and the second arm element in the connecting device around the screw. During this process, the spherical body of the first arm element rotates within the spherical cut-out of the first coupler. Likewise, the spherical body of the second arm element rotates within the spherical cut-out of the second coupler.

After finding the desired length of the cross-connector, the surgeon inserts a driver into the recess of the pin in the camming assembly and rotates the pin clockwise approximately 115 degrees to "lock" the pin in the first coupling assembly. When the pin is "locked," the ramped surfaces on the head of the pin have moved up the ramp in the aperture of the coupler; the first and second surfaces of the coupler are clamped around the spherical body of the first arm element; and the flange of the cam is pressed firmly against the rectangular recess in the tulip head, thereby securing the tulip head in place. The surgeon knows by feel that the pin is "locked" because the smaller semi-circular protrusion on the head of the pin is in smaller-semi-circular recess in the aperture of the coupler. The surgeon repeats this locking process with the camming assembly in the second coupling assembly.

To lock the center rotation of the cross-connector, the surgeon inserts a driver into the recess of the screw in the connecting device and rotates the screw clockwise until the threaded shank engages completely with the threaded region of the first arm element. The connecting device has a height above the center of the rod in the tulip head of a pedicle screw which allows the cross-connector to be placed above any features within the body.

In a second embodiment, the cross-connector is likewise sized and dimensioned for connecting to the tulip heads of pedicle screws on the same vertebral body. The cross-connector includes a first coupling assembly, a second coupling assembly, and a connecting device. The connecting device connects the coupling assemblies together and adjusts the overall length of the cross-connector. Both coupling assemblies have nearly identical (i.e. mirror image) features and functions. Each coupling assembly includes a coupler and a collet. The connecting device includes a first arm element, a second arm element, and a locking assembly.

Similar to the first embodiment of the cross-connector, the terms distal and proximal in the second embodiment are relative to the locking assembly in the connecting device. Distal refers to a location away from the locking assembly and proximal is an area closer to the locking assembly.

The coupler includes a first body portion and a second body portion. The first body portion includes an aperture and a side wall. The aperture is sized and dimensioned to fit around the tulip head of a pedicle screw. The side wall is generally curved to match the curvature of the walls of the tulip head. The size and shape of the aperture and the side wall give the coupler a low profile finish on the tulip head. A cylindrical protrusion, extends proximally from the side wall, and is sized and dimensioned for being received within the cylindrical recess in the tulip head.

The second body portion of the coupler makes an angle of 40 degrees with the first body portion and further includes an aperture, having a perimeter. The aperture is sized and dimensioned for receiving the cylindrical body of the first arm element, and is tapered from the distal end to the proximal end to provide a close fit with the collet. The perimeter is generally curved to allow the cylindrical body to rotate easily within the aperture.

The collet includes a first surface, a second surface, and an aperture, extending therebetween. The first surface includes a plurality of openings that extend to an area approximately three quarters of the distance from the first surface to the second surface. Similarly, the second surface includes a plurality of openings that extend to an area approximately three quarters of the distance from the second surface to the first surface. Both sets of openings are rectangular shaped and terminate at circular cut-outs to dissipate stresses within the collet. The collet has four openings on the first surface and four openings on the second surface, which alternate around the collet. This feature makes the collet flexible and allows the cylindrical body of the first arm element to rotate within the aperture of the collet.

The connecting device includes a first arm element, a second arm element, and a locking assembly.

The first arm element includes an elongated member, having a cylindrical body at the distal end and a rectangular body at the proximal end. By way of example only, the elongated member has an angle of 30 degrees to the horizontal. The cylindrical body is sized and dimensioned for fitting within the aperture of the collet and the aperture of the coupler.

The rectangular body of the first arm element includes an aperture that is sized and dimensioned for receiving the locking assembly in the connecting device. The rectangular body further includes a top, a bottom, and a first side, a second side, a third side, and a fourth side extending therebetween. The top is flat such that the head of the cap of the locking assembly rests on the top of the rectangular body when the cap is completely threaded with the base. The bottom has various features on the second and fourth sides which allow the rectangular body of the first arm element to move within the rectangular body of the second arm element.

The first side of the rectangular body connects to the elongated member. The second side includes teeth, contained within the aperture, and an elongated recess on the bottom. The teeth are sized and dimensioned for complimentary engagement with the teeth on the gear. The recess has a semi-cylindrical cross-sectional shape and is sized and dimensioned for receiving the elongated protrusion on the rectangular body of the second arm element. The length of the recess is longer than the elongated protrusion. The third side is parallel to the first side and connects the second side with the fourth side. The bottom of the fourth side includes a semi-cylindrical cross-sectional protrusion that is sized and dimensioned for moving within the elongated recess of the rectangular body of the second arm element.

Similar to the first arm element, the second arm element includes an elongated member, having a cylindrical body at the distal end and a rectangular body at the proximal end. The elongated member also has an angle of 30 degrees with the horizontal. The cylindrical body has identical features and functions as the cylindrical body of the first arm element.

The rectangular body of the second arm element includes an aperture that is sized and dimensioned for receiving the locking assembly. The second body further includes a top, a bottom, and a first side, second side, a third side, and fourth side extending therebetween. The top has various features on the second and fourth sides which allow the rectangular body of the second arm element to move within the rectangular body of the first arm element. The bottom is flat so that the bottom base of the locking device can easily move along the bottom of the rectangular body when the locking assembly rotates between the teeth of the first and second arm elements. Also, the flat bottom allows the bottom base of the locking device to press firmly against the rectangular body, thereby preventing lateral movement when the cap is completely threaded to the base.

The first side of the rectangular body of the second arm element connects with the elongated member. The second side includes an elongated protrusion on the top that has a semi-cylindrical cross-sectional shape and is dimensioned to move within the semi-cylindrical recess of the first arm element. The third side is parallel to the first side and connects the second side with the fourth side. The fourth side includes teeth, contained within the aperture, and a recess on the top. The teeth are sized and dimensioned for complimentary engagement with the teeth on the gear. The recess has a semi-cylindrical cross-sectional shape and is dimensioned for receiving the semi-cylindrical protrusion of the first arm element. The length of the recess is longer than the elongated protrusion.

The locking assembly includes a cap, a gear, and a base.

The cap includes a head and a shaft. The head further includes an aperture with a threaded region that extends the length of the shaft. The threaded region is sized and dimensioned to engage with the threaded shank of the base. The head has a torx shape for use with a driver, having a torx socket, to engage the cap with the base.

The gear includes an aperture and teeth along the outer surface of the aperture. The aperture further includes two protrusions. The aperture and protrusions are sized and dimensioned for fitting closely around the intermediate base of the base. The teeth are sized and dimensioned for cooperative engagement with the teeth of the first and second arm elements.

The base further includes a threaded shank, an intermediate base, and a bottom base. The threaded shank includes a recess which is sized and dimensioned for receiving a driver that allows the surgeon to rotate the gear between the first and second arm elements, thereby adjusting the overall length of the cross-connector. The intermediate base is disc shaped and includes flat surfaces that match with the protrusions in the gear. The bottom base is disc shaped. The intermediate base and bottom base are welded to the gear.

In use, the second embodiment of the cross-connector is applied after the pedicle screws and rods have been fully implanted in the spine. The cross-connector is then installed over the tulip heads of the pedicle screws. More specifically, a surgeon inserts the cylindrical protrusion of the first coupler into the cylindrical aperture in the tulip head of a first pedicle screw. The surgeon repeats this process to connect the second coupler to a tulip head on a second pedicle screw on the same vertebral body.

To determine the optimal length of the cross-connector, the surgeon inserts a driver into the recess of the base in the locking device to rotate the gear, which will move the first arm element and second arm element laterally. (The surgeon may also manually move the first and second arm elements.) When the gear rotates, the teeth of the gear will move within the teeth of the first and second arm elements. Additionally, the elongated protrusion on the bottom of the first arm element will move within the semi-cylindrical cross-sectional recess on the top of the second arm element, and the elongated protrusion on the top of the second arm element will move within the semi-cylindrical cross-sectional recess on the bottom of the first arm element.

To lock the lateral movement of the cross-connector, the surgeon places a driver around the head of the cap and rotates the cap clockwise until the threaded region of the cap is completely engaged with threaded shank of the base. At this point, the head of the cap will press down on the top of the rectangular body of the first arm element and the bottom base will press up against the bottom of the rectangular body of the second arm element. Thus, the gear will be prevented from moving within the teeth of the first and second arm elements. Finally, the cross-connector will have a height above the first and second couplers which allows the cross-connector to be placed above objects in the body.

The cross-connector in a third embodiment functions the same way and includes substantially the same structure as the cross-connector of the second embodiment. The cross-connector in the third embodiment has a different first coupler and second coupler in the first coupling assembly and the second coupling assembly respectively. The first and second couplers are hook shaped and snap directly onto a rod.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 10 is a cross-sectional view of the of the coupler of FIG. 4, showing the ramps for the pin in the camming assembly;

FIG. 11 is a perspective view of an example of a tulip head for use with the cross-connectors of FIG. 2 and FIG. 32;

FIG. 12 is a side view of the tulip head of FIG. 11;

FIG. 13 is a cross-sectional view of the tulip head of FIG. 12;

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The cross-connector disclosed herein boasts a variety of inventive features and components that warrant patent protection, both individually and in combination.

Figure 1:
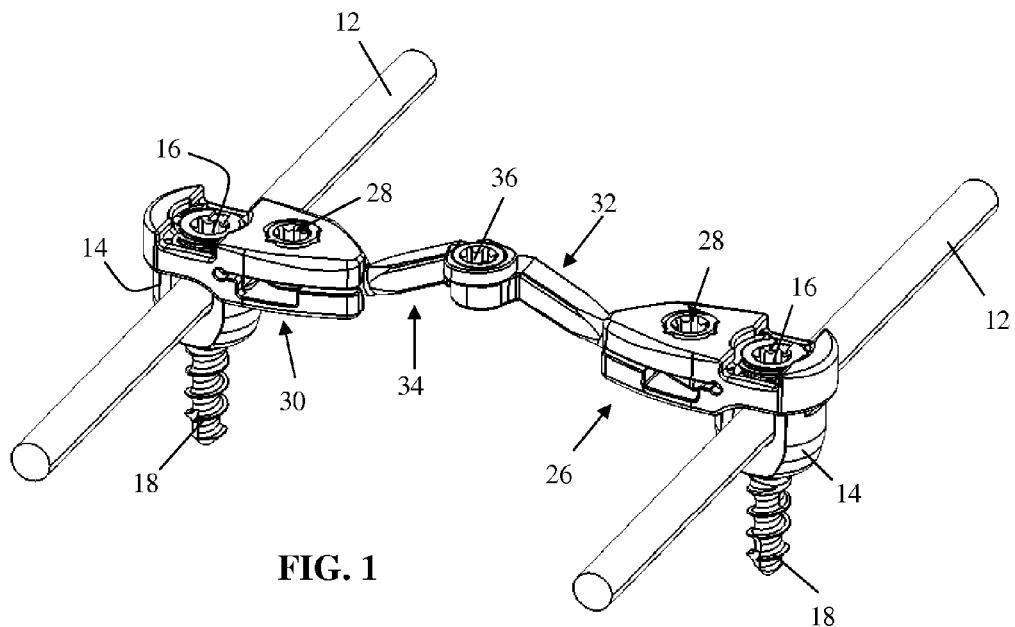
FIG. 1 is a front perspective view of an example of a cross-connector according to a first embodiment of the present invention, attached to the tulip heads of pedicle screws.
Figure 2:
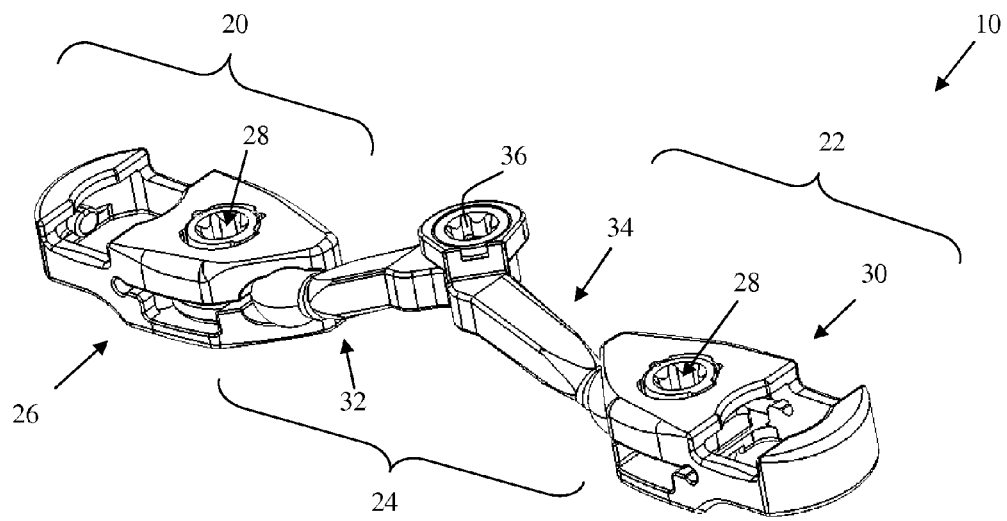
FIG. 2 is a rear perspective view of the cross-connector of FIG. 1.
Figure 3:
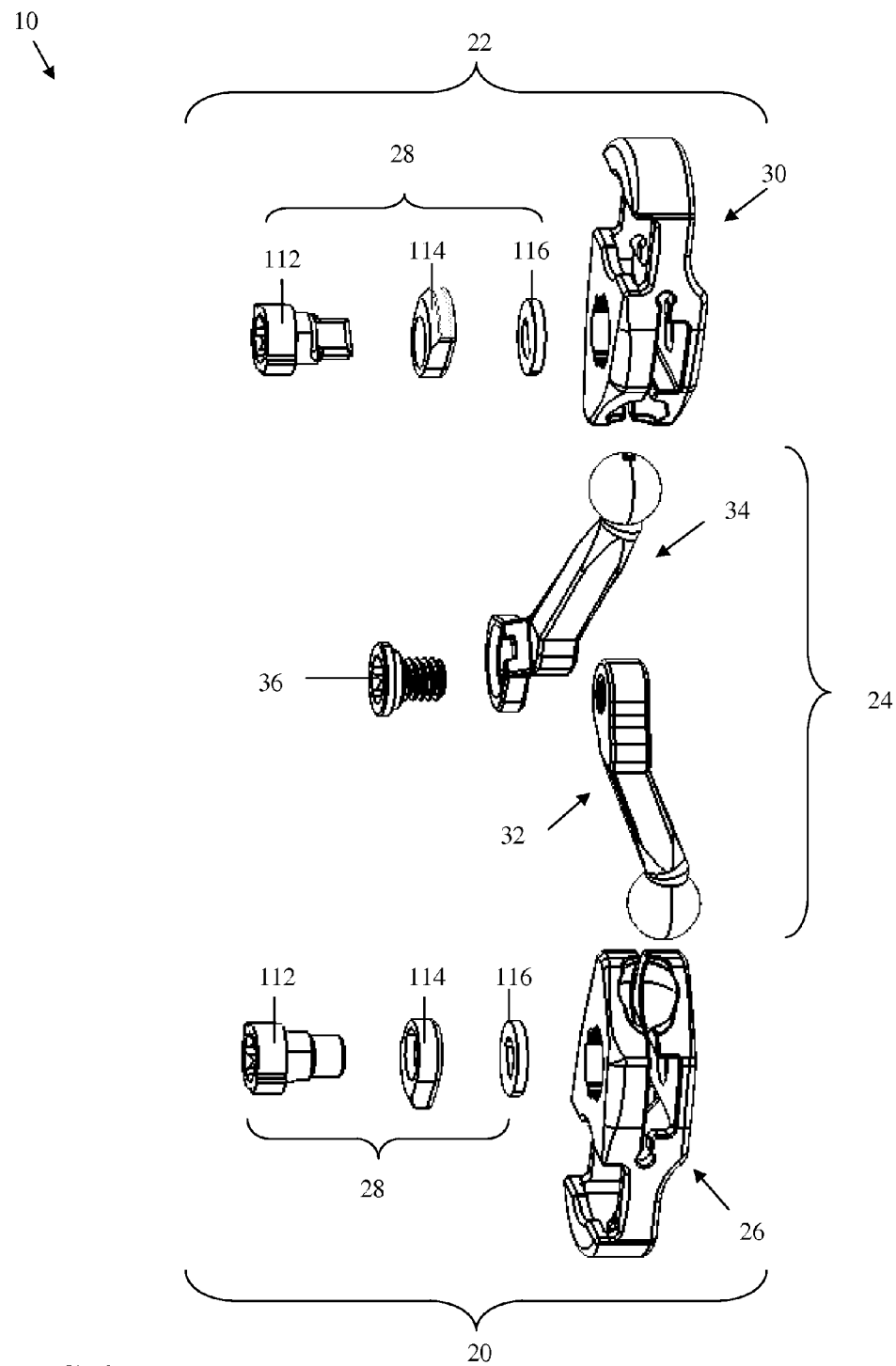
FIG. 3 is an exploded view of the cross-connector of FIG. 2.

FIGS. 1-3 illustrate an example of a cross-connector 10 according to a first embodiment of the present invention. The cross-connector 10 described herein is sized and dimensioned to connect to the tulip heads 14 of pedicle screws 18 on the same vertebral body. The cross-connector 10 includes a first coupling assembly 20, a second coupling assembly 22, and a connecting device 24 extending therebetween. As will be explained in further detail below, the first coupling assembly 20 attaches to a first tulip head 14 on a first pedicle screw 18, the second coupling assembly 22 attaches to a second tulip head 14 on a second pedicle screw 18, and the connecting device 24 allows a surgeon to adjust the overall length of the cross-connector 10.

The first coupling assembly 20 includes a first coupler 26 and a camming assembly 28. Similarly, the second coupling assembly 22 includes a second coupler 30 and a camming assembly 28. The connecting device 24 includes a first arm element 32, a second arm element 34, and a screw 36, connecting both arm elements together.

The first coupling assembly 20 will now be described in further detail with specific reference to FIGS. 4-20. It should be understood that the second coupling assembly 22 has nearly identical (e.g. mirror image) features and functions as the first coupling assembly 20, and therefore a repeat discussion is unnecessary. Referring first to FIGS. 4-10, the coupler 26 is generally a polygon shaped body 38, having a distal end 40 and a proximal end 42. The body 38 further includes a first body section 44 at the distal end 40 and a second body section 46 at the proximal end 42.

Figure 4:
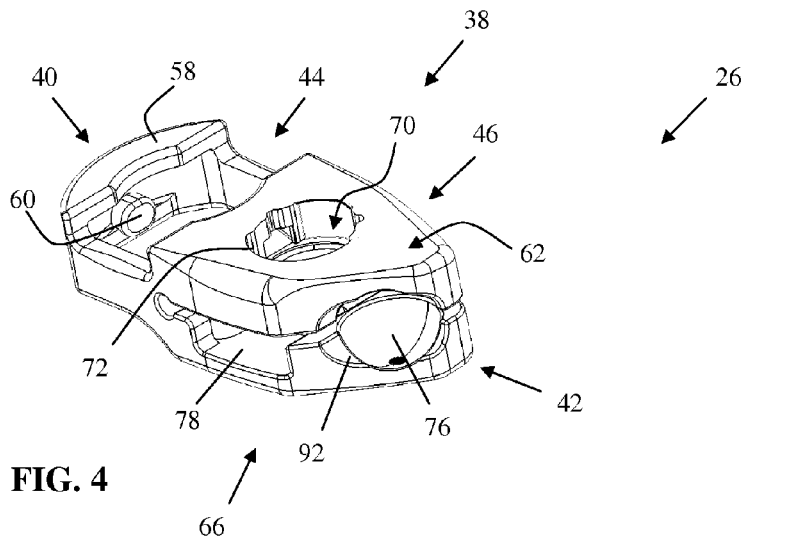
FIG. 4 is a side perspective view of a coupler forming part of the cross-connector of FIG. 2.
Figure 6:
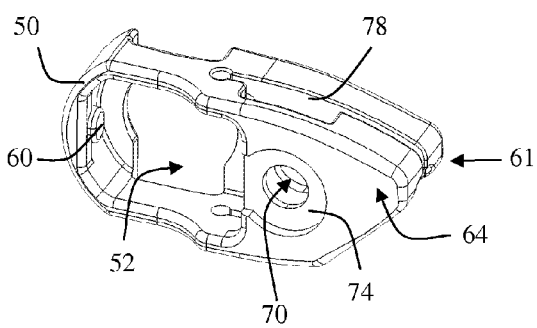
FIG. 6 is a bottom perspective view of the coupler of FIG. 4.

The first body section 44 of the coupler 26 includes a side wall 50 at the distal end 40 and an aperture 52, having a first edge 54 and a second edge 56. A surface 58 extends proximally from the side wall 50 and terminates at the first edge 54 of the aperture 52 (FIG. 4). The side wall 50 is generally curved and dimensioned to match the walls 100 of the tulip head 14, and includes a protrusion 60 that extends proximally from the side wall 50 (FIG. 6). By way of example only, the protrusion 60 generally has a cylindrical shape, sized and dimensioned for being received within the second recess 108 in the tulip head 14. The protrusion 60 also provides the first connection area between the coupler 26 and the tulip head 14. As will be described in more detail below, the flange 140 in the cam 114 in the camming assembly 28 in the second body section 46 provides the second connection area between the coupler 26 and the tulip head 14. The aperture 52, the first edge 54, and the second edge 56 are all sized and dimensioned for receiving the tulip head 14 and set screw 16 of a pedicle screw 18.

Figure 7:
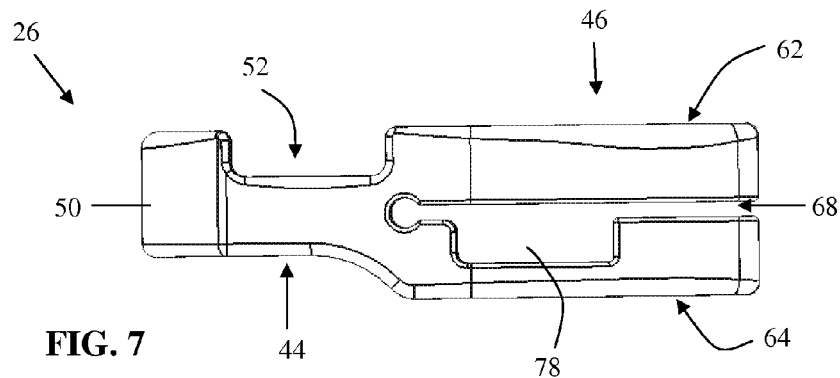
FIG. 7 is a first side view of the coupler of FIG. 4.

The second body section 46 of the coupler 26 extends proximally from the second edge 56 of the aperture 52 in the first body section 44. The second body section 46 includes a tip 61 at the proximal end 42, a first surface 62, a second surface 64, and a side surface 66, extending between the first surface 62 and the second surface 64. A space 68 separates the first surface 62 from the second surface 64 (FIG. 7). An aperture 70 extends through the second body section 46 from the first surface 62 to the second surface 64. The first surface 62 fomrs a perimeter 72 around the aperture 70. The second surface 64 includes a recess 74 surrounding the aperture 70. Side surface 66 includes a first cut-out 76 and a second cut-out 78.

Figure 30:
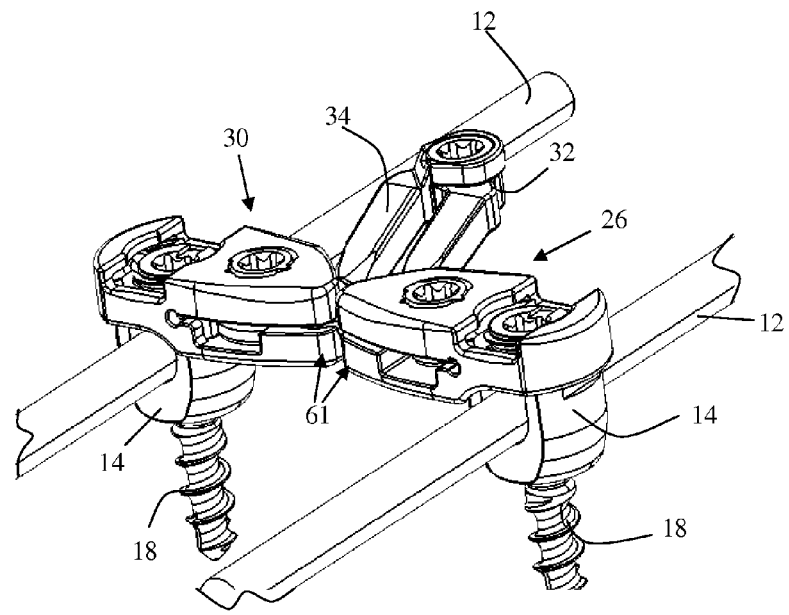
FIG. 30 is a side perspective view of the cross-connector of FIG. 1, showing the tips of the first coupler and second coupler in the same horizontal line.

The tip 61 at the proximal end 42 of coupler 26 generally has a flat surface for visual purposes and faces the tip 61 in the second coupler 30 in the same horizontal line (FIG. 30).

Figure 9:
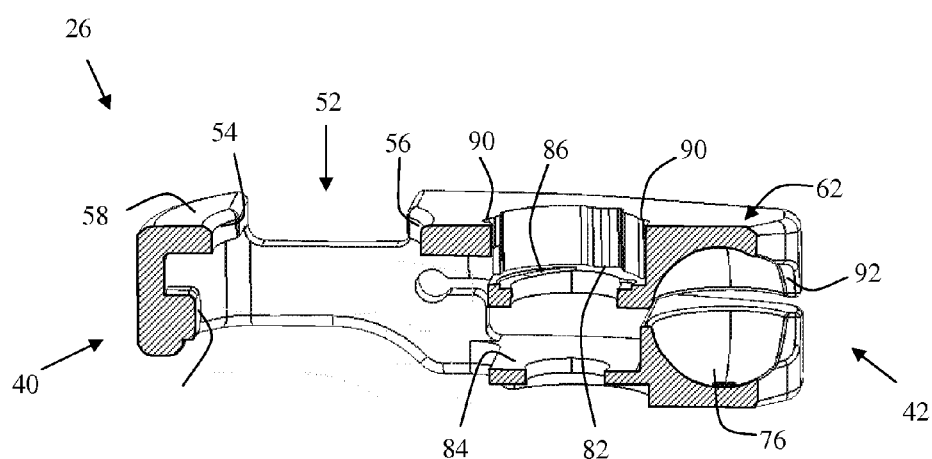
FIG. 9 is a side cross-sectional view of the coupler of FIG. 8.

The aperture 70 includes a first shelf 82 and second shelf 84 (FIG. 9). The first shelf 82 is located approximately midway through the aperture 70 between the first surface 62 and the second surface 64, and extends around the circumference of the aperture 70. The first shelf 82 includes two ramps 86 positioned on opposite sides of the aperture 70 from one another (FIGS. 9-10). The curvature of the ramps 86 corresponds with the generally ramped surfaces 130 on the pin 112 in the camming assembly 28. As the pin 112 is rotated, the ramped surfaces 130 engage the ramped will move up" one of the ramps 86 as it is rotated clockwise approximately 115 degrees to become "locked." When the pin 112 is "locked," the first surface 62 and the second surface 64 clamp around the first body 152 of the first arm element 32, and the flange 140 of the cam 114 presses against the first recess 106 in the tulip head 14.

Figure 14:
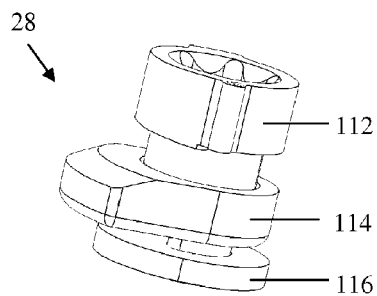
FIG. 14 is a perspective view of the camming assembly forming part of the cross-connector of FIG. 2.
Figure 15:
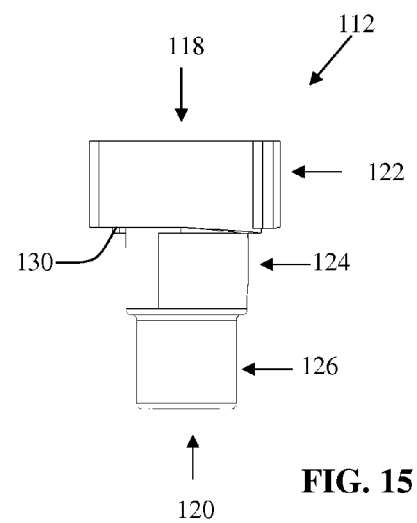
FIG. 15 is a first side view of a pin forming part of the camming assembly of FIG. 14.
Figure 16:
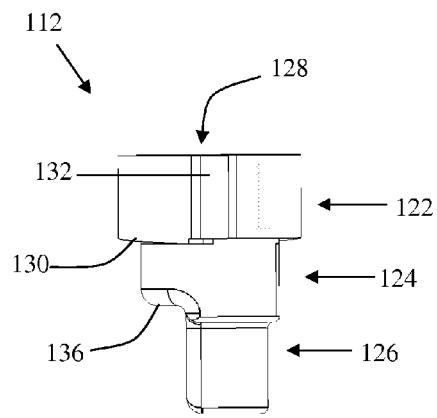
FIG. 16 is a second side view of the pin of FIG. 15.

The second shelf 84 in the aperture 70 is located about three quarters of the distance from the first surface 62 to the second surface 64, and extends around the circumference of the aperture 70. The second shelf 84 supports the cam 114 in the camming assembly 28 when the pin 112 rotates the cam 114. The aperture 70 terminates within a recess 74 that is sized and dimensioned for receiving the weld cap 116 of the camming assembly 28 on the second surface 64 (FIG. 14).

Figure 5:
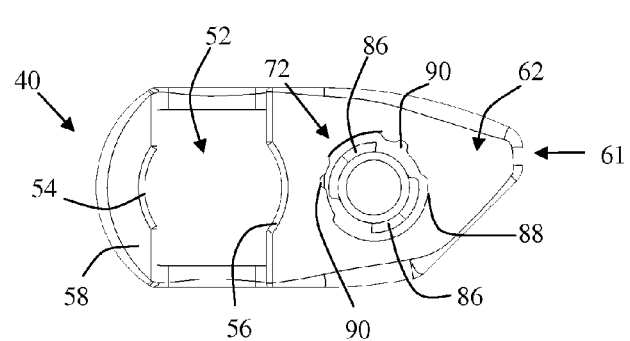
FIG. 5 is a plan view of the coupler of FIG. 4.
Figure 17:
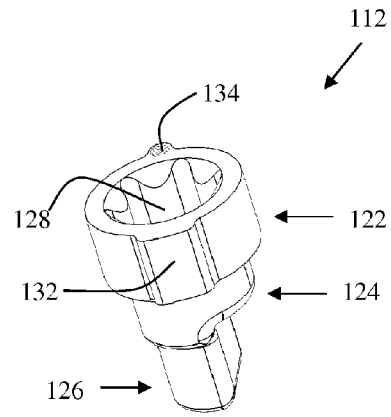
FIG. 17 is a perspective view of the pin of FIG. 15.
Figure 18:
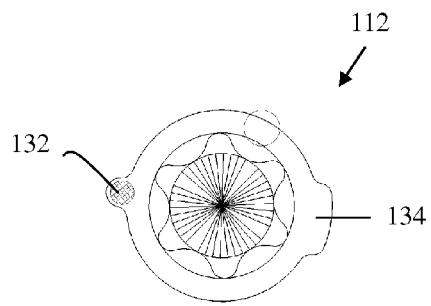
FIG. 18 is a plan view of a head portion of the pin of FIG. 15.

Referring to FIGS. 4-5, the perimeter 72 of the aperture 70 includes a first recess 88 and second recess 90, both of which generally have semi-circular shapes. First recess 88 and second recess 90 correspond with the first protrusion 132 and second protrusion 134 on the head 122 of the pin 112 of the camming assembly 28 (FIG. 17). The first recess 88 generally has a larger diameter than the second recess 90, and guides the first protrusion 132 as the pin 112 moves up the ramp 86. As the pin 112 finishes rotating 115 degrees or reaches the top of the ramp 86, the second protrusion 134 becomes positioned within the second recess 90. This positioning will be the result of a snap fit engagement between the second protrusion 134 and the second recess 90. Thus, the surgeon knows by feel that the pin 112 is locked and that this rotation is complete.

Figure 8:
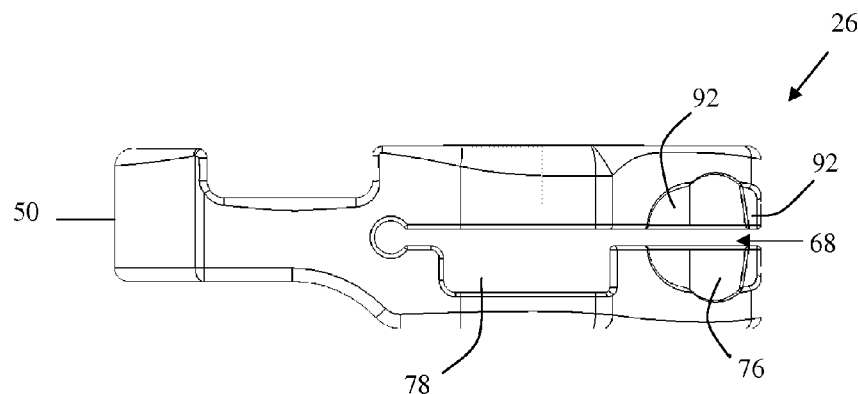
FIG. 8 is a second side view of the coupler of FIG. 4.

The side surface 66 of the second body section 46 of the coupler 26 will now be described in detail (FIGS. 4, 8, 10). The first cut-out 76 is generally spherical in shape and dimensioned to receive the first body 152 at the distal end of the first arm element 32. The first cut-out 76 acts like a ball joint by providing the greatest degree of movement for the body 152 when the surgeon is adjusting the length of the connecting device 24. Additionally, the first cut-out 76 has smaller generally spherical cut-outs 92, surrounding the first cut-out 76. Adjacent to the smaller spherical cut-outs 92 is the second cut-out 78, having a generally rectangular shape. The second cut-out 78 and the smaller cut-outs 92 provide extra flexibility to the coupler 26 when the first surface 62 and second surface 64 of the coupler 26 clamp to the spherical body 152 of the first arm element 32.

The space 68 between the first surface 62 and second surface 64 of the coupler 26 also provides flexibility to the coupler 26 when the spherical body 152 of the first arm element 32 rotates within the first cut-out 76 when the surgeon is adjusting the length of the connecting device 24.

Figure 29:
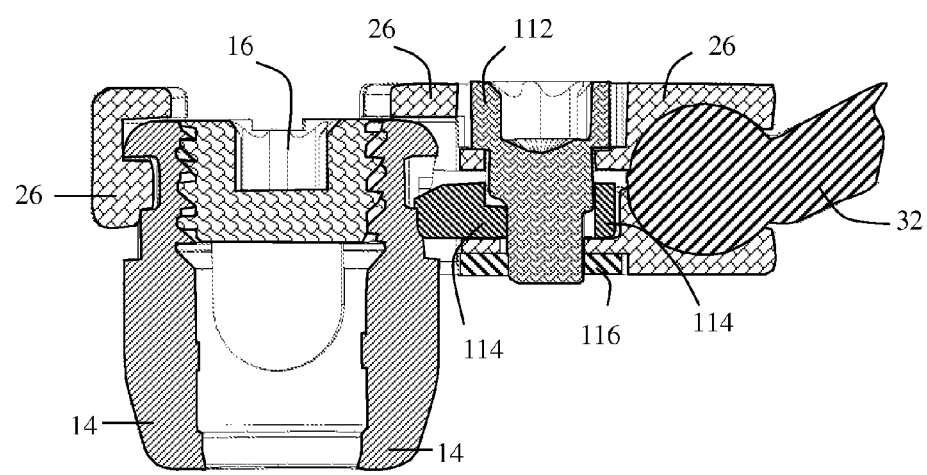
FIG. 29 is side cross-sectional view of the tulip head and coupler of FIG. 1, showing a cam that is pressing against a tulip head.

Referring to FIG. 11-13, the tulip head 14 used with the first embodiment of the cross-connector 10 and the second embodiment of the cross-connector 210 will now be described in detail. The tulip head 14 includes a U-shaped body 94, having a top 96 and a bottom 98. The body 94 is dimensioned for receiving a rod 12, and further includes walls 100 and an aperture 102. One of the walls 100 has a cut-out 104 at top 96 for visual purposes to allow the surgeon to line up the set screw 16 with the body 94 of the tulip head 14. Both walls 100 have a first recess 106 that includes a second recess 108. By way of example only, the first recess 106 generally has a rectangular shape and provides an area where the flange 140 of the cam 114 presses against the tulip head 14, thereby locking the tulip head 14 in place (FIG. 29). The second recess 108 is generally cylindrical in shape and dimensioned to receive the protrusion 60 in the coupler 26. Finally, the aperture 102 has a threaded region 110 at the top 96, which is sized and dimensioned for receiving a set screw 16 that connects the rod 12 to the tulip head 14.

Referring to FIGS. 14-20, the camming assembly 26 will now be described in detail. The camming assembly 26 is located within aperture 70 of the second body section 46 of the coupler 26, and includes a pin 112, a cam 114, and a weld cap 116. The pin 112 rotates the cam 114, The weld cap 116 resides in the recess 74 and is welded to the pin 112 in order to keep the cam assembly assembled and force the second surface 64 upwards when the cam is rotated to the "locked" position to inhibit movement of the arm element 32, as described below.

The pin 112, shown in FIGS. 15-18, further includes a top 118 and a bottom 120, having a head 122, a middle section 124, and a stem 126 extending between the top 118 and the bottom 120. The head 122 includes a recess 128 at the top of the head 122, ramped surfaces 130 at the bottom of the head 122, and a first protrusion 132 and second protrusion 134, extending therebetween. The recess 128 is sized and dimensioned for receiving a driver (not shown) to allow the surgeon to rotate the pin 112 and the cam 114. The ramped surfaces 130 at the bottom of the head are separated by 180 degrees and correspond with the curvature of the ramps 86 in the coupler 26. By way of example only, the first protrusion 132 and the second protrusion 134 are generally semi-circular in shape and match the shape of the first recess 88 and second recess 90 respectively on the perimeter 72 of the aperture 70. The first protrusion 132 generally has a larger diameter than the second protrusion 134.

The middle section 124 of the pin 112 includes a step 136 that is sized and dimensioned to fit above the shelf 146 in the cam 114. The step 136 rotationally fixes the cam 114 to the pin such that rotation of the pin 112 also rotates the cam. Finally, the stem 126 is sized and dimensioned to fit within aperture 144 of the cam 114 and the aperture 148 of the weld cap 116.

Figure 19:
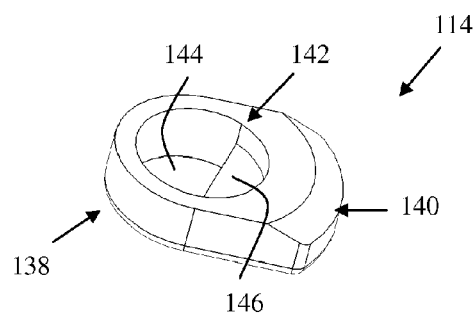
FIG. 19 is a side perspective view of a cam forming part of the camming assembly of FIG. 14.

The cam 114, shown in FIG. 19, includes a curved body 138, having a flange 140. The curved body 138 further includes a generally circular opening 142, having an aperture 144 and a shelf 146. While the opening 142 is sized and dimensioned for receiving both the middle section 124 and the stem 126 of the pin 112, the aperture 144 can generally accommodate only the stem 126. The diameter of the aperture 144 is generally larger than the diameter of the stem 126 to allow the cam 114 to move easily around the stem 126. The flange 140 is generally curved so that the cam 114 can easily move along the curved walls 100 of the tulip head 14 before pressing against the first recess 106 in the tulip head 14, thereby providing the second area of contact between the coupler 26 and the tulip head 14.

Figure 20:
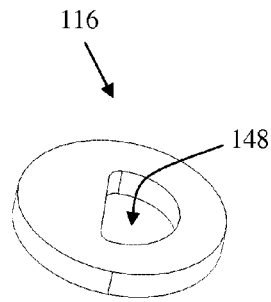
FIG. 20 is a side perspective view of a weld cap forming part of the camming assembly of FIG. 14.

The weld cap 116, shown in FIG. 20, is generally disk shaped and sized and dimensioned for fitting within the recess 74 in the second surface 64 of the coupler 26. Furthermore, the weld cap 116 includes an aperture 148 that is sized and dimensioned to contain the stem 126 of the pin 112.

According to an alternate embodiment, the cam assembly may be replaced with a set screw. The position and size of the set screw may be such that when the set screw is advanced through the aperture 70 (which in this embodiment is threaded) the screw prevents the tulip head from moving such that the protrusion 60 cannot disengage from the recess 108). Additionally, the set screw may only thread into the second surface 64 and include a flange that rests above the first surface 62 such that tightening the setcrew also squeezes the first and second surfaces together to inhibit movement of the arm element 32.

Referring to FIGS. 21-27, the connecting device 24 will now be described in further detail. The connecting device 24 includes a first arm element 32, a second arm element 34, and a screw 36.

Figure 21:
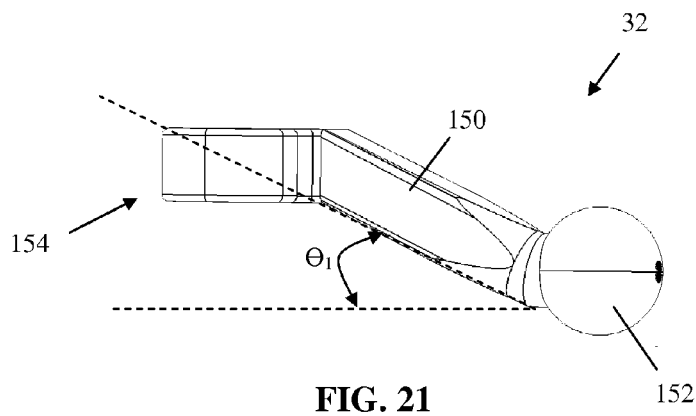
FIG. 21 is a side view of a first arm element forming part of the connecting device of FIG. 2.
Figure 22:
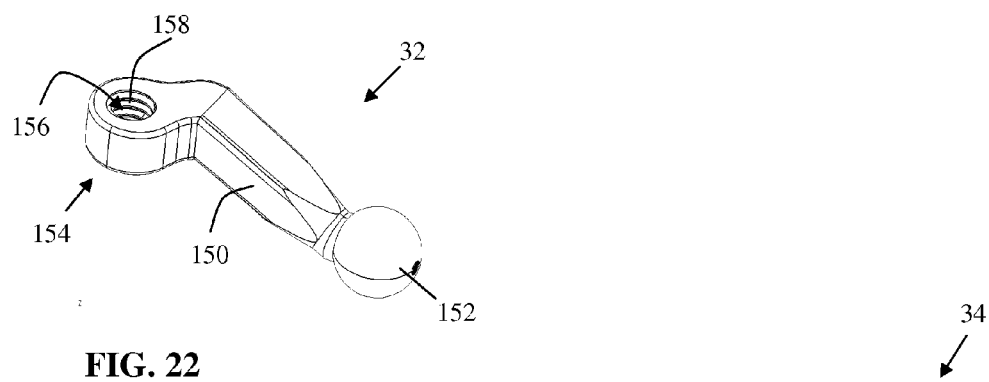
FIG. 22 is a side perspective view of the first arm element of FIG. 21.

The first arm element, shown in FIGS. 21-22, includes an elongated member 150, having a first body 152 at the distal end, and a second body 154 at the proximal end. The elongated member 150 makes an angle, $\theta_1$, with the horizontal. While $\theta_1$ can range from zero degrees to 45 degrees, $\theta_1$ is 27 degrees in the preferred embodiment. The first body 152 has a spherical shape, which is sized and dimensioned to rotate within the cut-out 76 in the coupler 26 when the surgeon adjusts the length of the connecting device 24. The second body 154 is generally disk shaped and includes an aperture 156 extending therethrough. The aperture 156 includes a threaded region 158. Both the aperture 156 and the threaded region 158 are sized and dimensioned for receiving the threaded shank 178 of the screw 36. Though not shown, according to another embodiment, the first body 152 may have a partially spherical shape with one or more flats to limit movement in one or more planes.

Figure 23:
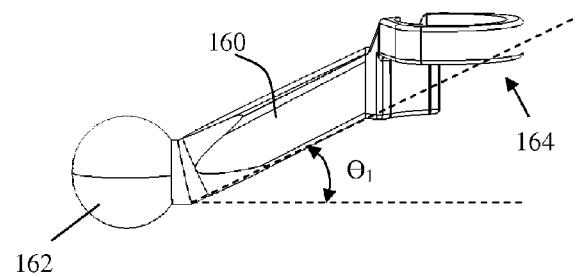
FIG. 23 is a side view of a second arm element forming part of the connecting device of FIG. 2.
Figure 24:
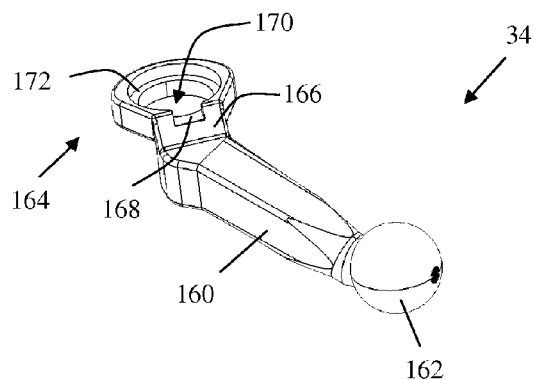
FIG. 24 is a side perspective view of the second arm element of FIG. 23.

Similar to the first arm element 32, the second arm element 34, shown in FIGS. 23-24, includes an elongated member 160, having a first body 162 at the distal end and a second body 164 at the proximal end. An angled surface 166, with a cut-out 168 for stability, extends between the elongated member 160 and the second body 164. The elongated member 160 also makes an angle, $\theta_1$, with the horizontal. The first body 162 has a spherical shape, which is sized and dimensioned to rotate within the cut-out 76 in the coupler 26 when the surgeon adjusts the length of the connecting device 24. Though not shown, according to another embodiment, the first body 162 may have a partially spherical shape with one or more flats to limit movement in one or more planes.

The second body 164 is generally disk shaped and includes an aperture 170 extending therethrough. The aperture 170 includes a shelf 172 that extends around the circumference of the aperture 170. Both the aperture 170 and the shelf 172 are sized and dimensioned for receiving the head 174 of the screw 36. The angled surface 166 extends the overall length of the second arm element 34 so that the second body 164 rests vertically above the second body 154 of the first arm element 32, and the screw 36 can lock the second body 154 of the first arm element 32 and second body 164 of the second arm element 34 together (FIG. 27).

Figure 25:
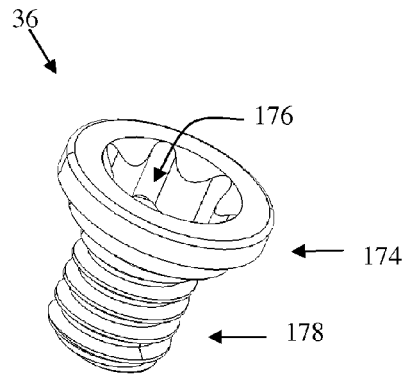
FIG. 25 is a side perspective view of a pin forming part of the connecting device of FIG. 2.
Figure 26:
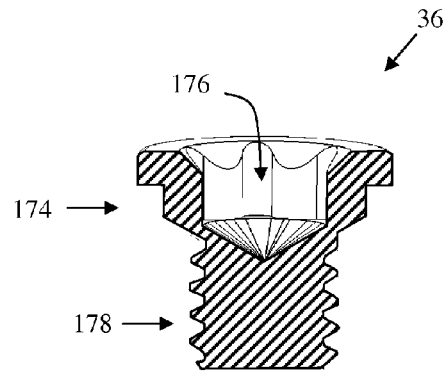
FIG. 26 is a side cross-sectional view of the pin of FIG. 25.
Figure 27:
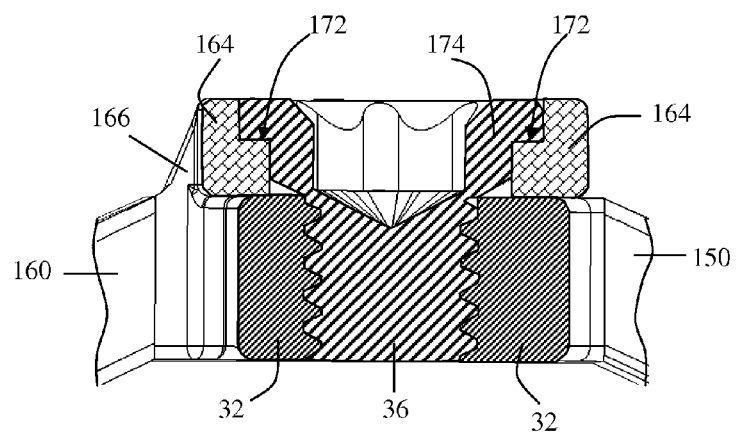
FIG. 27 is a side cross-sectional view of the connecting device of FIG. 2, illustrating where the pin connects with the first arm element and second arm element.

Referring to FIGS. 25-27, the screw 36 includes a head 174, having a recess 176, and a threaded shank 178. The head 174 is generally rounded and dimensioned to pass through the aperture 170 in the second arm element 34. The recess 176 is sized and dimensioned for receiving a driver (not shown) which allows a surgeon to engage the threaded shank 178 with the threaded region 158 of the first arm element 32. When the threaded shank 178 is completely engaged with the threaded region 158, the cross-connector will not be able to rotate in the center and the head 174 will rest on the shelf 172 in the aperture 170 of the second arm element 34 (FIG. 27).

The screw 36 acts as a center pivot point for the connecting device 24 where the first arm element 32 and second arm element 34 move around the screw 36 to adjust the overall length of the cross-connector 10. Although the first arm element 32 and the second arm element 34 can pivot 45 degrees in one direction and 45 degrees in the opposite direction around the screw 36, this range of movement is limited to 20 degrees in both directions in the preferred embodiment. Furthermore, this angular movement of the first arm element 32 and the second arm element 34 allows a surgeon to place the connecting device 24 around any features within the body.

In one embodiment of the cross-connector 10, the overall length has a range of 28-44 mm inclusive. A second embodiment has a range of 38-50 mm inclusive.

Figure 28:
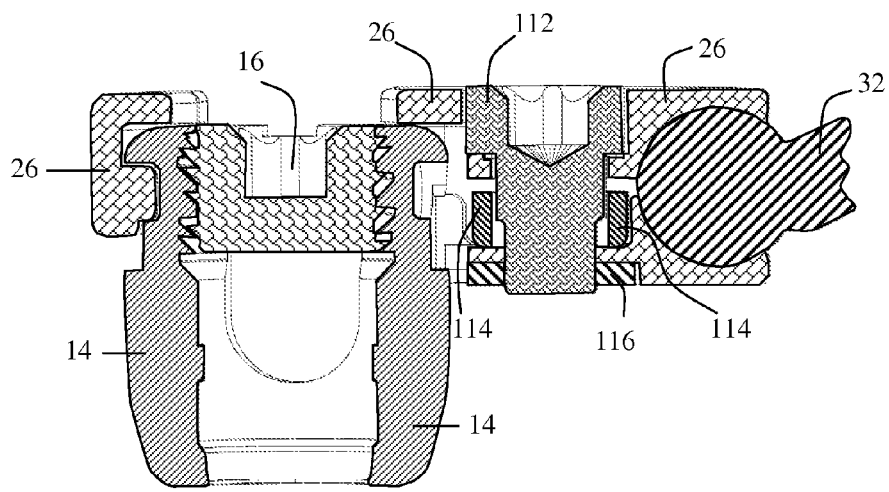
FIG. 28 is a side cross-sectional view of the tulip head and coupler of FIG. 1, showing a cam that is not pressing against the tulip head.

In use, the cross-connector 10 is applied after the pedicle screws 18 and rods 12 have been fully implanted in the spine. The cross-connector 10 is then installed over the tulip heads 14 of the pedicle screws 18. More specifically, the surgeon inserts the cylindrical protrusion 60 of the first coupler 26 into the cylindrical aperture 108 in the tulip head 14 of a first pedicle screw 18 (FIG. 28). The surgeon repeats this process to connect the second coupler 30 to a tulip head 14 on a second pedicle screw 18 on the same vertebral body. At this point, the tip 80 of the first coupler 26 will be in the same horizontal line as the tip 80 of the second coupler 30. The tips 80 will remain in the same horizontal line even when the surgeon adjusts the length of the cross-connector 10 (FIG. 30).

To determine the optimal length of the cross-connector 10, a surgeon pivots the first arm element 32 and the second arm element 34 in the connecting device 24 around the screw 36. During this process, the spherical body 152 of the first arm element 32 will rotate within the spherical cut-out 76 of the first coupler 26. Likewise, the generally spherical first body portion 162 of the second arm element 34 rotates within the spherical cut-out 76 of the second coupler 30.

After finding the desired length of the cross-connector 10, the surgeon inserts a driver (not shown) into the recess 128 of the pin 112 in the camming assembly 28 and rotates the pin 112 clockwise approximately 115 degrees to "lock" the pin 112 in the first coupling assembly 20. When the pin 112 is "locked," the ramped surfaces 130 on the head 122 of the pin 112 have moved up the ramp 86 in the aperture 70 of the coupler 26; the first surface 62 and the second surface 64 of the coupler 26 are clamped around the generally spherical first body portion 152 of the first arm element 32; and the flange 140 of the cam 114 is pressed firmly against the rectangular aperture 106 in the tulip head 14, thereby securing the tulip head 14 into place (FIG. 29). Furthermore, the surgeon knows by feel that the pin 112 is "locked" because the smaller semi-circular protrusion 132 on the head 122 of the pin 112 will be in smaller semi-circular recess 90 in the aperture 70 of the coupler 26. The surgeon repeats this locking process with the camming assembly 28 in the second coupling assembly 22.

Figure 31:
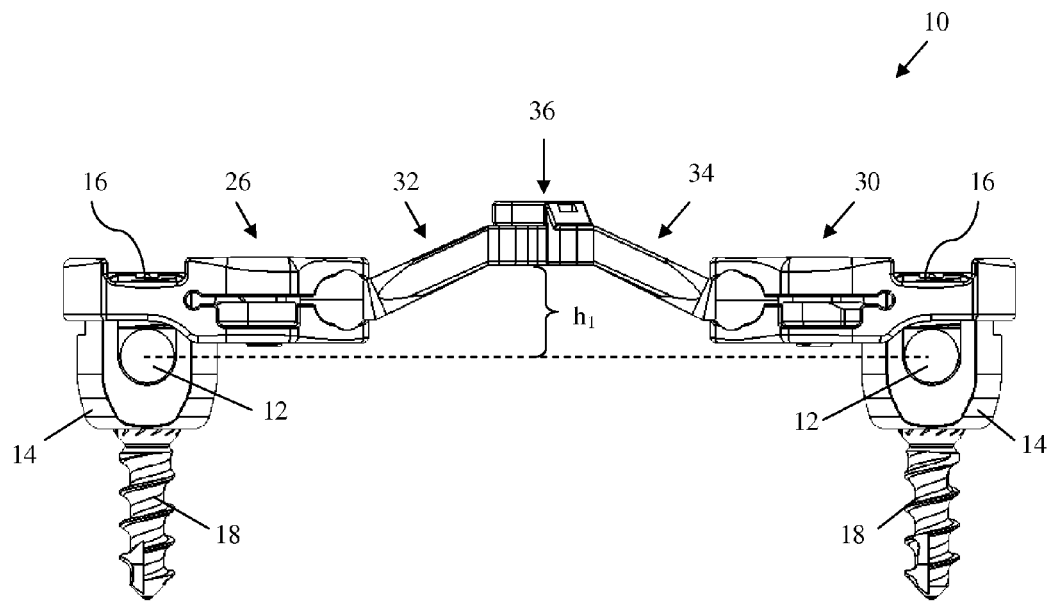
FIG. 31 is a side view of the cross-connector of FIG. 1, showing the height, $h_1$, of the cross-connector above the center of the rods contained within pedicle screws.

Finally, to lock the center rotation of the cross-connector 10, the surgeon inserts a driver (not shown) into the recess 176 of the screw 36 in the connecting device 24 and rotates the screw 36 clockwise until the threaded shank 178 engages with the threaded region 158 of the first arm element 32. The connecting device 24 has a height, $h_1$, above the center of the rod 12 in the tulip head 14 of a pedicle screw 18, which allows the cross-connector 10 to be placed above any features within the body (FIG. 31).

FIGS. 32-53 illustrate an example of a cross-connector 210 according to a second embodiment of the present invention. The cross-connector 210 includes similar features to the cross-connector 10, and is likewise sized and dimensioned for connecting to the tulip heads 14 of pedicle screws 18 on the same vertebral body. The cross-connector 210 includes a first coupling assembly 212, a second coupling assembly 214, and a connecting device 216. The connecting device 216 connects the first coupling assembly 212 together with the second coupling assembly 214, and adjusts the overall length of the cross-connector 210. The first coupling assembly 212 includes a coupler 218 and a collet 220. Similarly, the second coupling assembly 214 also includes a coupler 222 and collet 224. The connecting device 216 includes a first arm element 226, a second arm element 228, and a locking assembly 229.

The first coupling assembly 212 will now be described in further detail with specific reference to FIGS. 34-39. It should be understood that the second coupling assembly 214 has nearly identical (e.g. mirror image) features and functions as the first coupling assembly 212, and therefore a repeat discussion is unnecessary.

Figure 34:
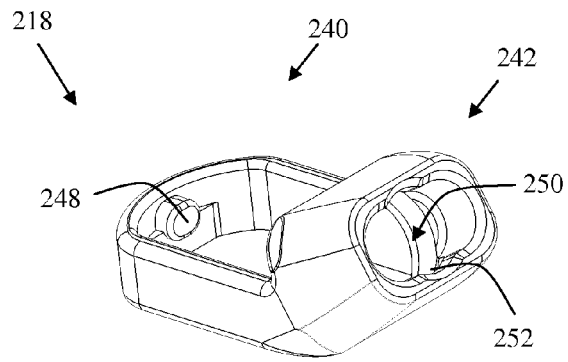
FIG. 34 is a side view of a coupler forming part of the first coupling assembly of FIG. 33.
Figure 35:
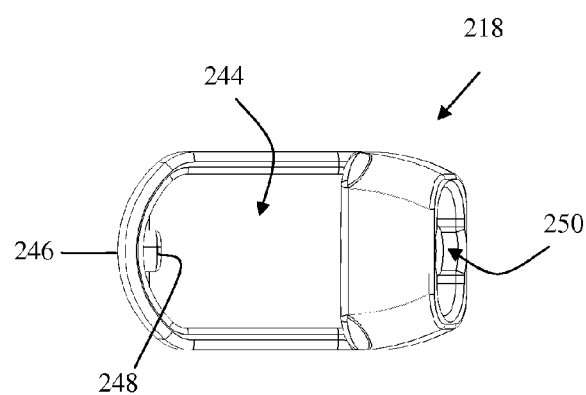
FIG. 35 is a plan view of the coupler of FIG. 36.

Referring first to FIGS. 34-35, the coupler 218 includes a first body portion 240 and a second body portion 242. The first body portion 240 includes an aperture 244 and a side wall 246. The aperture 244 is sized and dimensioned to fit around the tulip head 14 of a pedicle screw 18. The side wall 246 is generally curved to match the curvature of the walls 100 of the tulip head 14. The size and shape of the aperture 244 and the side wall 246 give the coupler 218 a low profile finish on the tulip head 14. A protrusion 248, generally cylindrical in shape, extends proximally from the side wall 246, and is sized and dimensioned for being received within the cylindrical aperture 108 in the tulip head 14.

Figure 38:
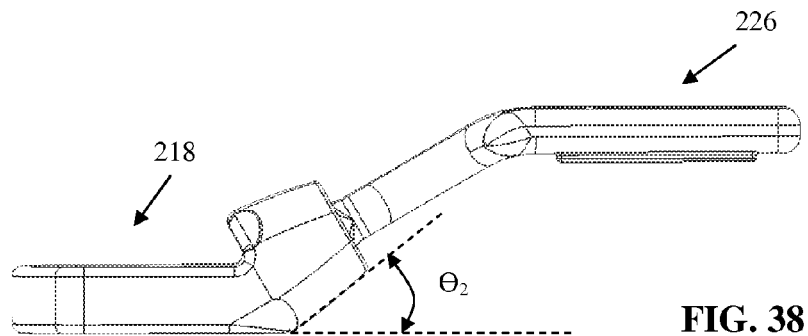
FIG. 38 is a side perspective view of the first coupling assembly and the first arm element forming part of the cross-connector of FIG. 32.
Figure 39:
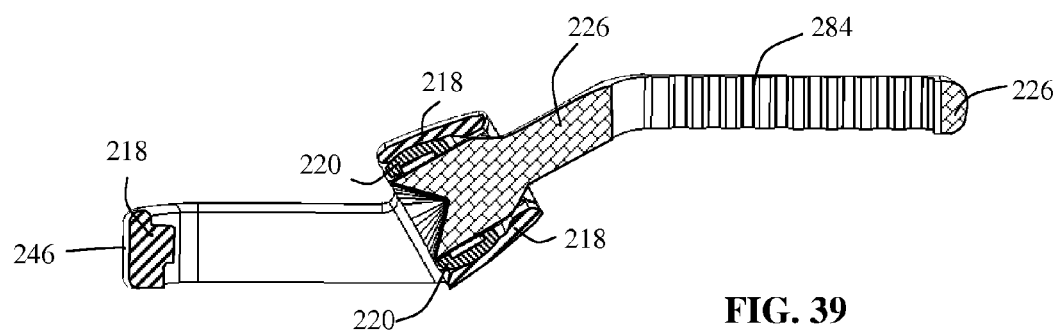
FIG. 39 is a cross-sectional view of the first coupling assembly and first arm element of FIG. 38.
Figure 40:
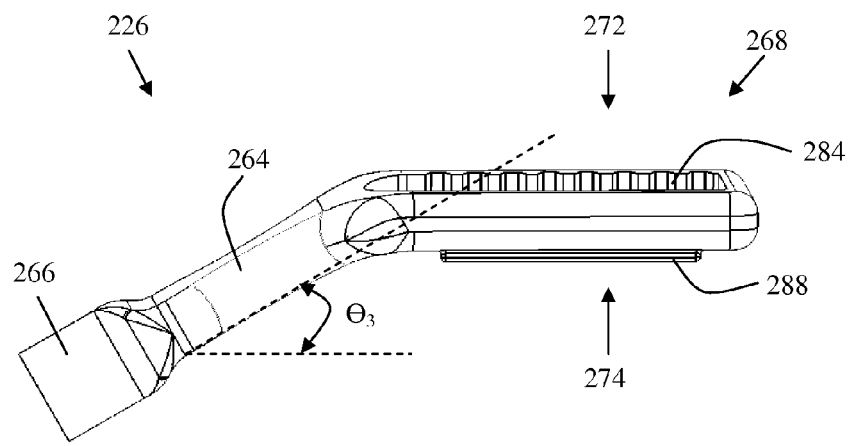
FIG. 40 is a side view of the first arm element in the connecting device of FIG. 33.
Figure 41:
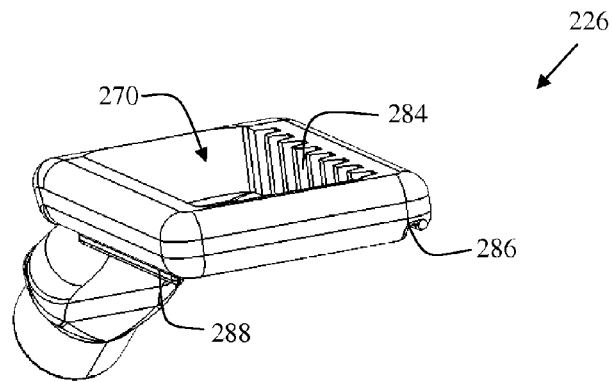
FIG. 41 is a perspective view of the first arm element of FIG. 40.

The second body portion 242 of the coupler 18 makes an angle, $\theta_2$, with the first body portion 240, and further includes an aperture 250, having a perimeter 252 (FIG. 38). While $\theta_2$ ranges from 0 degrees to 60 degrees, $\theta_2$ has a value of 40 degrees in the preferred embodiment. The aperture 250 is sized and dimensioned for receiving the first body portion 266 of the first arm element 226, and is tapered from the distal end to the proximal end to provide a close fit with the collet 220 (FIG. 39). The perimeter 252 is generally curved to allow the first body 266 to rotate easily within the aperture 250. The tapered first body portion 266 works with the collet 220 to inhibit movement between the coupler 218 and the first arm element 226. That is, as the arm element 226 pulls away from the collet 224 during adjustment, the tapered end 266 forces the collet 224 against the inside walls of the aperture 250, deforming the collet and locking locking the arm element 226. According to an alternate embodiment, The arm element 226 can be locked with a set screw advanced through the coupler 218 to crush the collet 224

Figure 36:
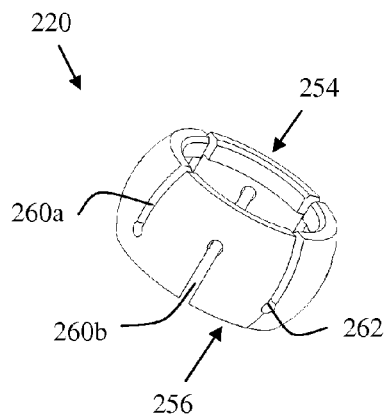
FIG. 36 is a perspective view of a collet forming part of the coupling assembly of FIG. 33.
Figure 37:
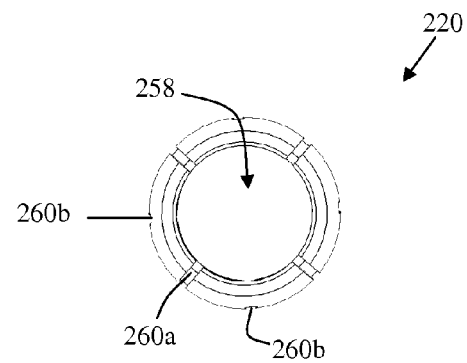
FIG. 37 is a plan view of the collet of FIG. 38.

The collet 220, shown in FIGS. 36-37, includes a first surface 254, a second surface 256, and an aperture 258, extending therebetween. The first surface 254 further includes a plurality of openings 260a that extend to an area approximately three quarters of the distance from the first surface 254 to the second surface 256. Similarly, the second surface 256 further includes a plurality of openings 260b that extend to an area approximately three quarters of the distance from the second surface 256 to the first surface 254. The openings (260a and 260b) are generally rectangular shaped and terminate at generally circular cut-outs 262, to dissipate stresses within the collet 220. The collet 220 has equal numbers of openings 260a and openings 260b, which alternate around the collet 220. By way of example only, the collet 220 shown here has a total of eight openings (260a and 260b), but collets 220 having more or less than this value of openings are possible without departing from the scope of this invention. This feature makes the collet 220 flexible and allows the first body 266 of the first arm element 226 to rotate within the aperture 258 of the collet 220.

The connecting device 216 includes a first arm element 226, a second arm element 228, and a locking assembly 229.

Referring to FIGS. 40-43, the first arm element 226 will now be described in detail. The first arm element 226 includes an elongated member 264, having a first body 266 at the distal end and a second body 268 at the proximal end. The elongated member 264 in the cross-connector 210 makes an angle, $\theta_3$, with the horizontal. Although $\theta_3$ has a range of zero to 60 degrees, $\theta_3$ has a value of 30 degrees in the preferred embodiment. The first body 266 is generally cylindrical in shape and is sized and dimensioned for fitting within the aperture 258 of the collet 220 and the aperture 250 of the coupler 218.

The second body 268 of the first arm element 226 is generally rectangular in shape, and includes an aperture 270 that is sized and dimensioned for receiving the locking assembly 229 in the connecting device 216. The second body 268 further includes a top 272, a bottom 274, and a first side 276, a second side 278, a third side 280, and a fourth side 282 extending therebetween. The top 272 of the second body 268 is flat such that the head 318 of the cap 230 of the locking assembly 229 rests on the top 272 of the second body 268 when the cap 230 is completely threaded with the base 234. The bottom 274 has various features on the second side 278 and fourth side 282 which allow the second body 268 to move within the second body 294 of the second arm element 228, as will be explained below.

Figure 42:
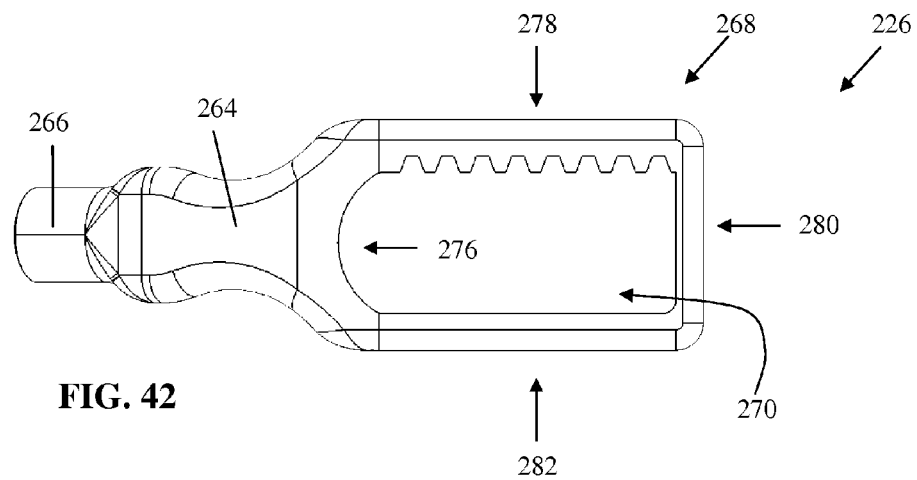
FIG. 42 is plan view of the top of the first arm element of FIG. 41.
Figure 43:
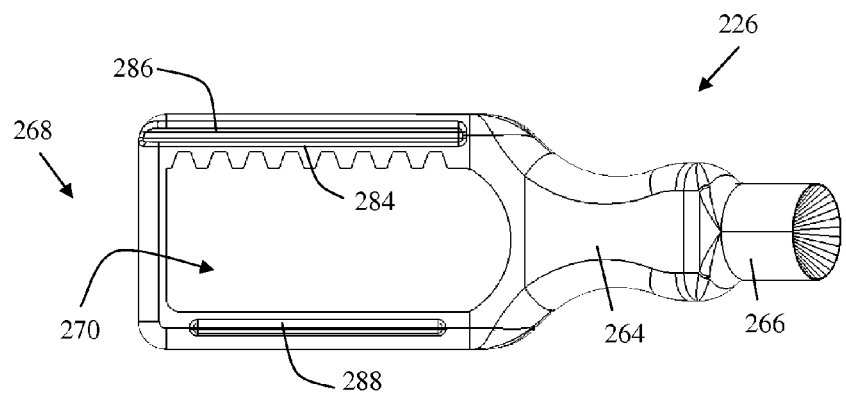
FIG. 43 is plan view of the bottom of the first arm element of FIG. 41.
Figure 44:
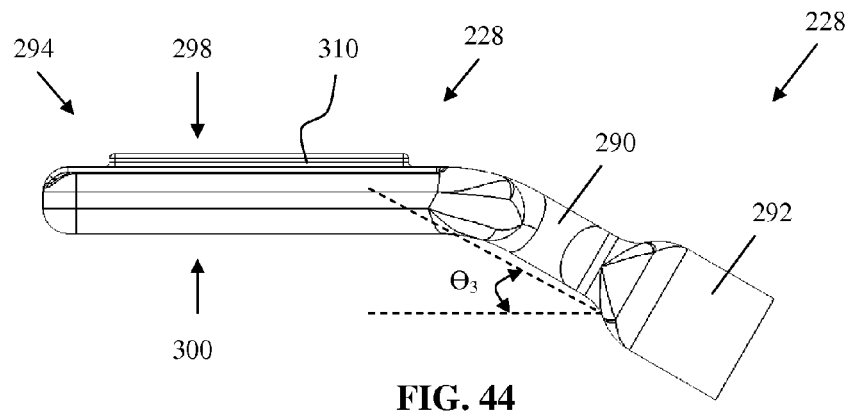
FIG. 44 is a side view of the second arm element in the connecting device of FIG. 33.
Figure 45:
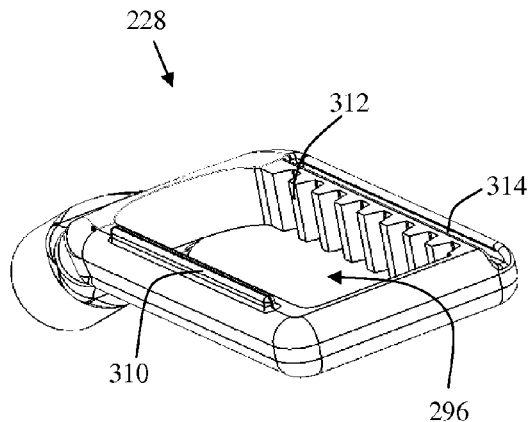
FIG. 45 is a perspective view of the second arm element of FIG. 44.

Referring now to FIGS. 42-43, the first side 276 of the second body 268 connects to the elongated member 264. The second side 278 includes teeth 284, contained within the aperture 270, and an elongated recess 286 on the bottom 274. The teeth 284 are sized and dimensioned for complimentary engagement with the teeth 328 on the gear 232. The recess 286 generally has a semi-cylindrical cross-sectional shape and is sized and dimensioned for receiving the elongated protrusion 310 of the second body portion 294 of the second arm element 228. The length of the recess 286 is longer than the elongated protrusion 310. The third side 280 is parallel to the first side 276 and connects the second side 278 with the fourth side 282. The fourth side 282 includes a protrusion 288 on the bottom 274. The protrusion 288 has a semi-cylindrical cross-sectional shape and is sized and dimensioned for moving within the recess 314 of the second body 294 of the second arm element 228.

Referring now to FIGS. 44-47, the second arm element 228 of the second coupling assembly 214 will now be described in detail. Similar to the first arm element 226, the second arm element 228 includes an elongated member 290, having a generally cylindrical first body portion 292 at the distal end and a generally rectangular second body portion 294 at the proximal end. The elongated member 290 also has an angle $\theta_3$ with the horizontal. The first body 292 of the second arm element 228 has identical features and functions as the first body 266 of the first arm element 226.

The second body 294 of the second arm element 228 includes an aperture 296 that is sized and dimensioned for receiving the locking assembly 229 in the connecting device 216. The second body 294 further includes a top 298, a bottom 300, and a first side 302, second side 304, a third side 306, and a fourth side 308 extending therebetween (FIGS.

46-47). The top 298 has various features on the second side 304 and the fourth side 308 which allow the second body portion 294 to move within the second body portion 268 of the first arm element 226. The bottom 300 of the second body 294 is flat so that the bottom base 336 of the locking device 216 can easily move along the bottom 300 when the locking assembly 229 rotates between the teeth 284 of the first arm element 226 and the teeth 312 of the second arm element 228. Also, the flat bottom 300 allows the bottom base 336 of the locking device 229 to press firmly against the second body portion 294, thereby preventing lateral movement when the cap 230 is completely threaded to the base 234.

Figure 46:
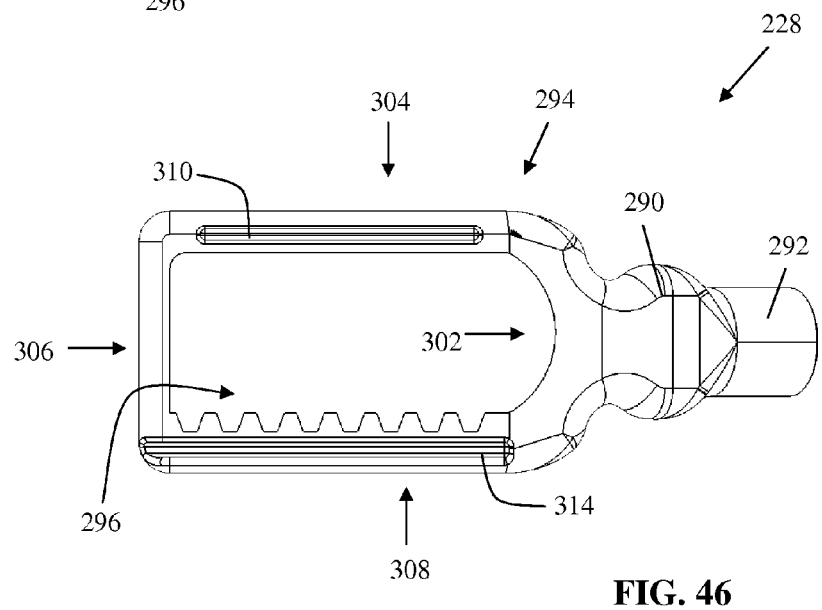
FIG. 46 is a plan view of the top of the second arm element of FIG. 45.
Figure 47:
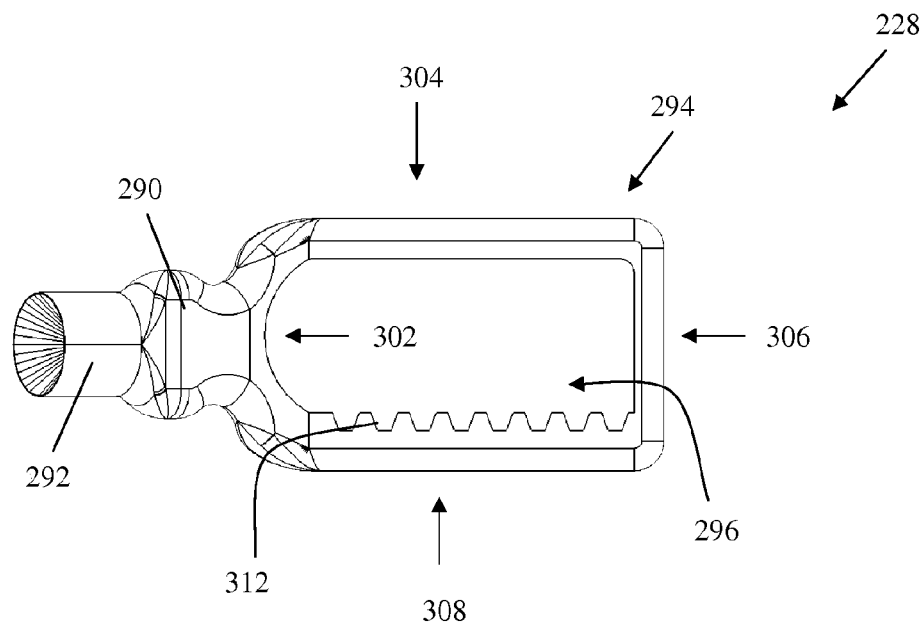
FIG. 47 is plan view of the bottom of the second arm element of FIG. 45.
Figure 48:
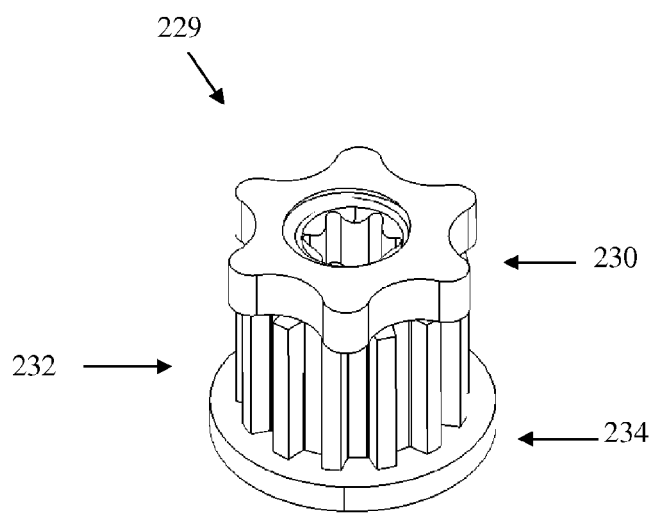
FIG. 48 is a front perspective view of a locking assembly forming part of FIG. 32.

Referring now to FIGS. 46-47, the first side 302 of the second body 294 connects with the elongated member 290. The second side 304 includes an elongated protrusion 310 on the top 298 that has a semi-cylindrical cross-sectional shape and is dimensioned to move within the semi-cylindrical recess 286 of the first arm element 226. The third side 306 is parallel to the first side 302 and connects the second side 304 with the fourth side 308. The fourth side 308 includes teeth 312, contained within the aperture 296, and a recess 314 on the top 298. The teeth 312 are sized and dimensioned for complimentary engagement with the teeth 328 on the gear 232. The recess 314 has a semi-cylindrical cross-sectional shape and is dimensioned for receiving the semi-cylindrical protrusion 288 of the first arm element 226. The length of the recess 314 is generally longer than the elongated protrusion 288.

Referring now to FIGS. 48-51, the locking assembly 229 will now be described in detail. The locking assembly 229 includes a cap 230, a gear 232, and a base 234.

Figure 49:
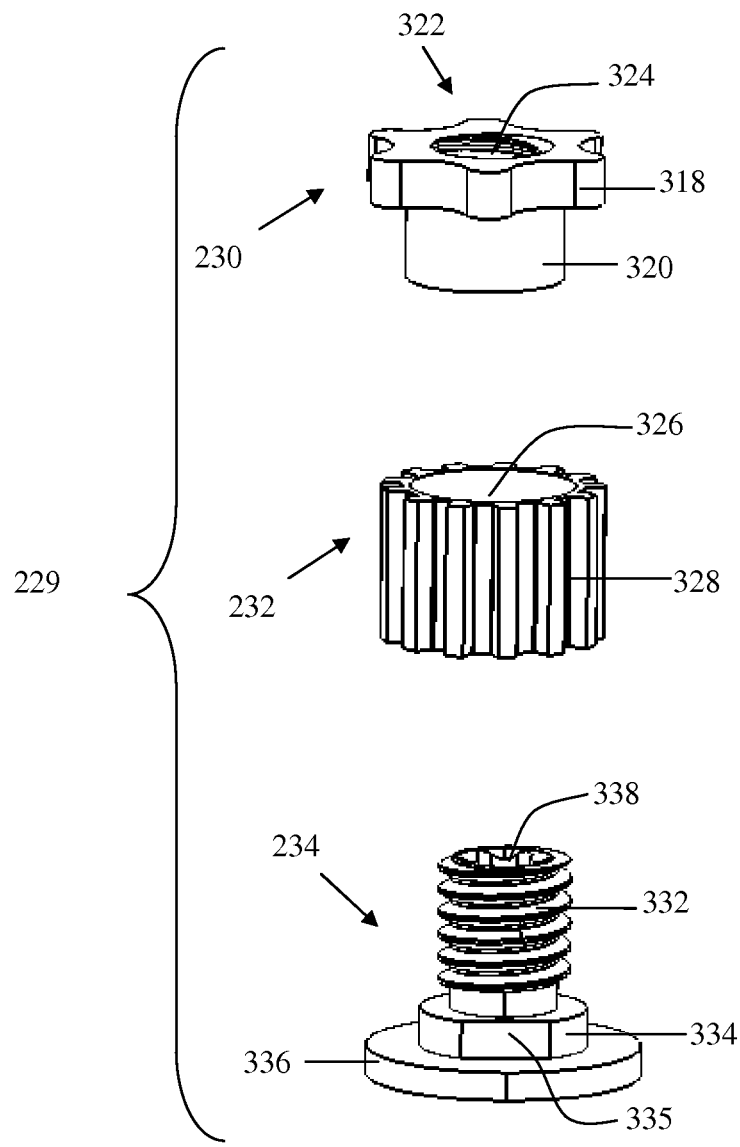
FIG. 49 is an exploded view of the locking assembly of FIG. 48.

The cap 230 includes a head 318 and a shaft 320. The head 318 further includes an aperture 322 with a threaded region 324 that extends the length of the shaft 320 (FIG. 49). The threaded region 324 is sized and dimensioned to engage with the threaded shank 332 of the base 234. By way of example only, the head 318 shown here has a torx shape for use with a driver, having a torx socket, to engage the cap 230 with the base 234. It should be noted that other shapes of the head 318 and corresponding drivers are possible without departing from the scope of this invention.

Figure 50:
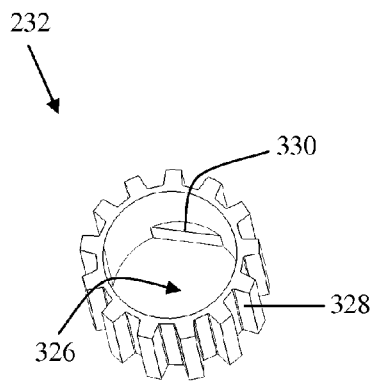
FIG. 50 is a perspective view of a gear forming part of the locking assembly of FIG. 49.
Figure 51:
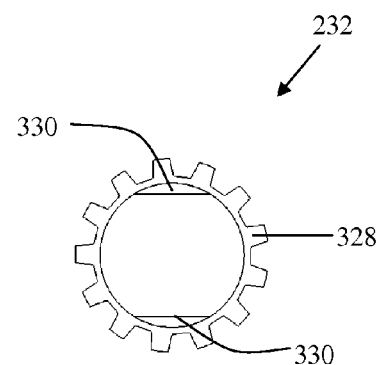
FIG. 51 is a plan view of the gear of FIG. 49.

The gear 232 further includes an aperture 326 and teeth 328 along the outer surface of the aperture 326. The aperture 326 also includes two protrusions 330 (FIG. 50-51). The aperture 326 and protrusions 330 are sized and dimensioned for fitting closely around the intermediate base 334 of the base 234. The teeth 328 are sized and dimensioned for cooperative engagement with the teeth 284 of the first arm element 226 and the teeth 312 of the second arm element 228.

The base 234 further includes a threaded shank 332, an intermediate base 334, and a bottom base 336. The threaded shank 332 includes a recess 338 which is sized and dimensioned for receiving a driver (not shown) that allows the surgeon to rotate the gear 232 between the first arm element 226 and second arm element 228, thereby adjusting the overall length of the cross-connector 210. The intermediate base 334 is generally disc shaped and includes flat surfaces 335 that match with the protrusions 330 in the gear 232. The bottom base 336 is also generally disc shaped. The intermediate base 334 and bottom base 336 are welded to the gear 232.

In use, the cross-connector 210 is applied after the pedicle screws 18 and rods 12 have been fully implanted in the spine. The cross-connector 210 is then installed over the tulip heads 14 of the pedicle screws 18. More specifically, a surgeon inserts the protrusion 248 of the first coupler 218 into the second aperture 108 in the tulip head 14 of a first pedicle screw 18. The surgeon repeats this process to connect the second coupler 222 to a tulip head 14 on a second pedicle screw 18 on the same vertebral body.

Figure 52:
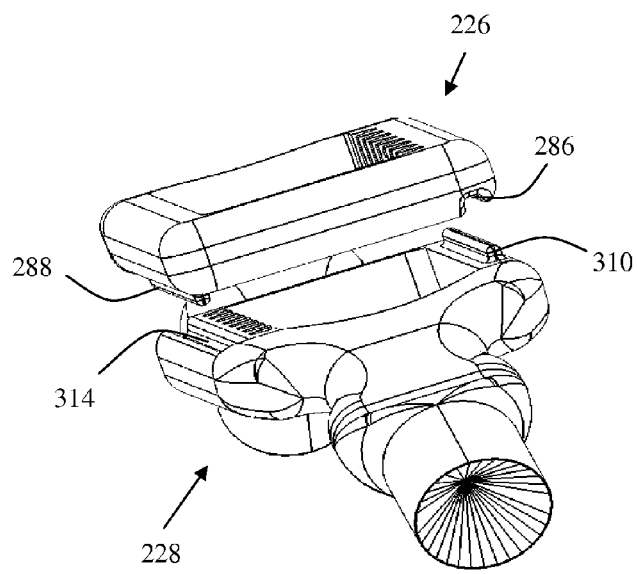
FIG. 52 is an exploded perspective view of the connecting region between the first arm element and second arm element of FIG. 32 without the locking assembly.

To determine the optimal length of the cross-connector 210, a surgeon inserts a driver (not shown) into the recess 338 of the base 234 in the locking devices 216 to rotate the gear 232, which will move the first arm element 226 and second arm element 228 laterally. When the gear 232 rotates, the teeth 328 of the gear 232 will move within the teeth 284 of the first arm element 226 and the teeth 312 of the second arm element 228. Additionally, the protrusion 288 on the bottom 274 of the first arm element 226 will move within the recess 314 on the top 298 of the second arm element 228, and the protrusion 310 on the top 298 of the second arm element 228 will move within the recess 286 on the bottom 274 of the first arm element 226 (FIG. 52).

Figure 32:
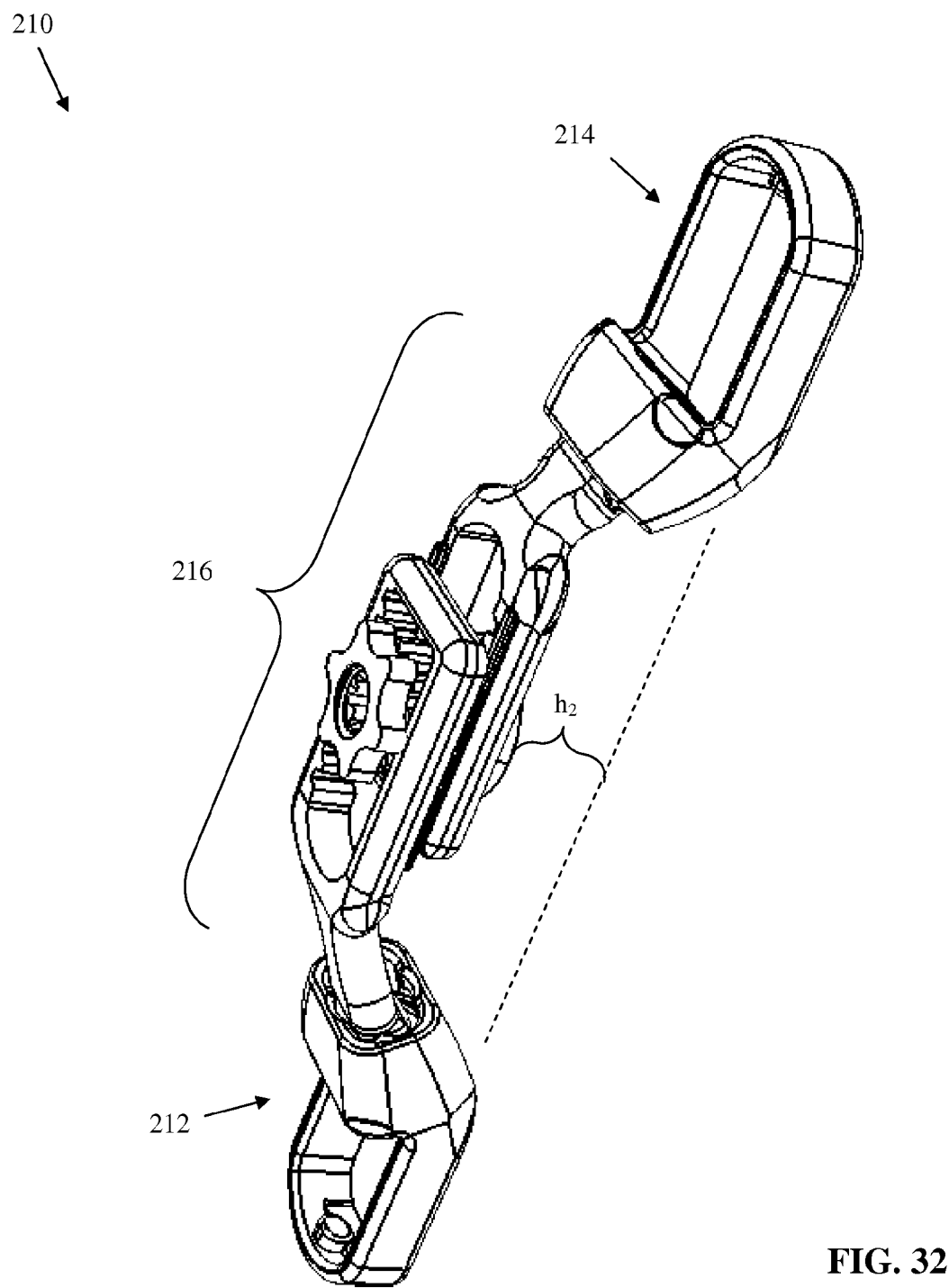
FIG. 32 is a side perspective view of an example of a cross-connector according to a second embodiment of the present invention.
Figure 33:
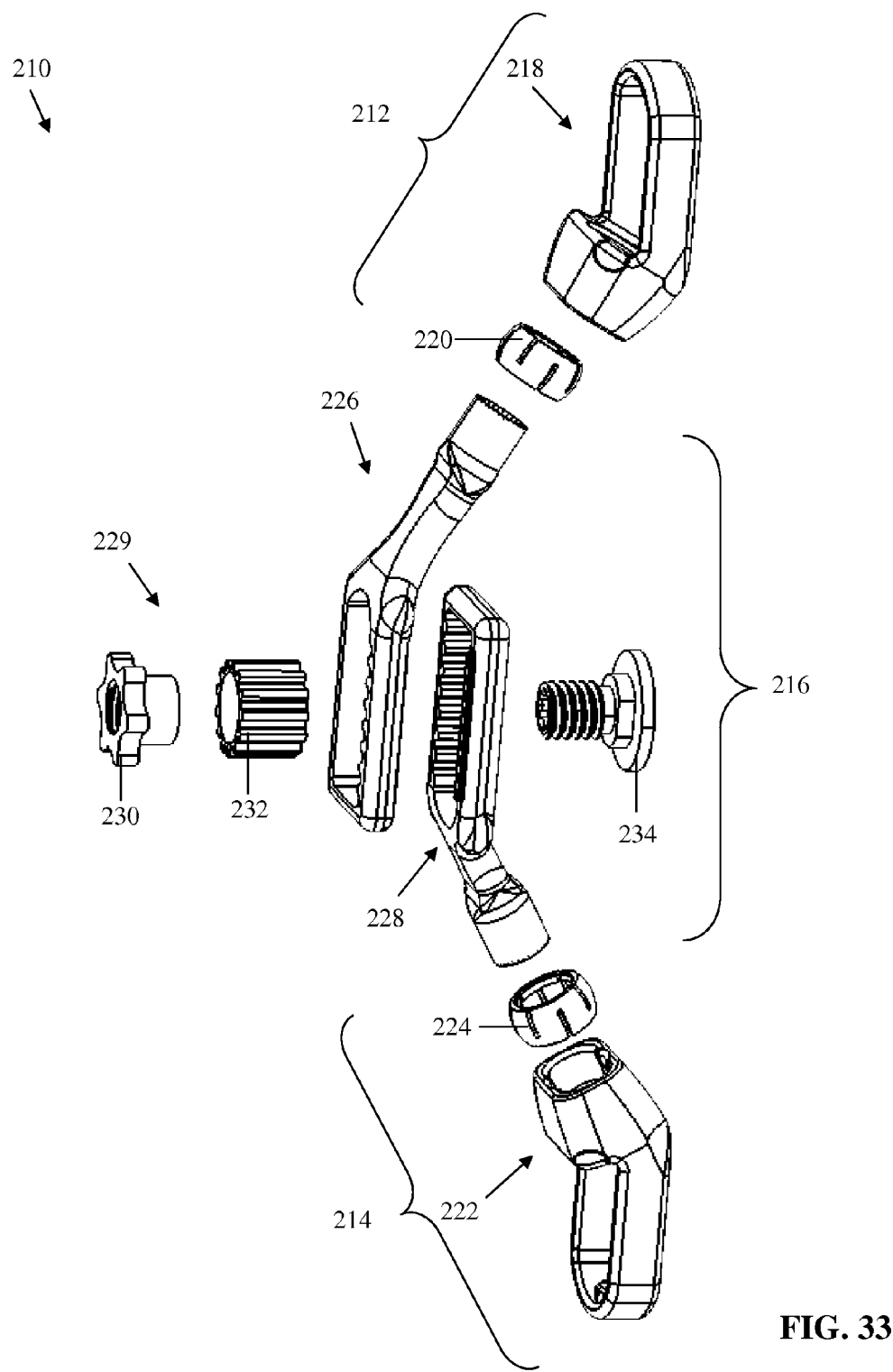
FIG. 33 is an exploded view of the cross-connector of FIG. 32.
Figure 53:
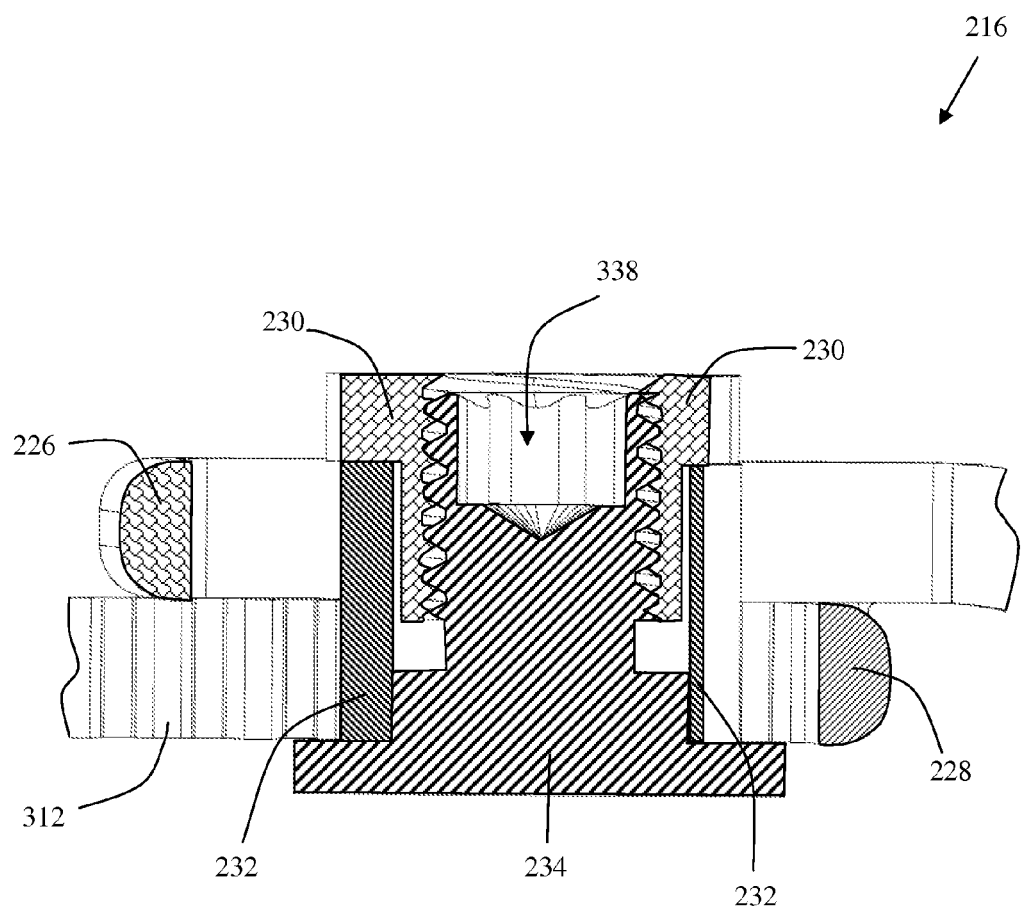
FIG. 53 is a cross-sectional view of the region where the locking assembly connects with the first arm element and the second arm element of FIG. 32.

To lock the lateral movement of the cross-connector 210, the surgeon places a driver (not shown) around the head 318 of the cap 230 and rotates the cap 230 clockwise until the threaded region 324 of the cap is completely engaged with threaded shank 332 of the base 234. At this point, the head 318 of the cap 230 will press down on the top 272 of the rectangular body 268 of the first arm element 226 and the bottom base 336 will press up against the bottom 300 of the rectangular body 294 of the second arm element 228. Thus, the gear 232 will be prevented from moving within the teeth 284 in the first arm element 226 and the teeth 312 in the second arm element 228 (FIG. 53). Finally, the cross-connector 210 will have a height, $h_2$, above the first coupler 218 and second coupler 222, which allows the cross-connector 210 to be placed above objects in the body (FIG. 32).

Figure 54:
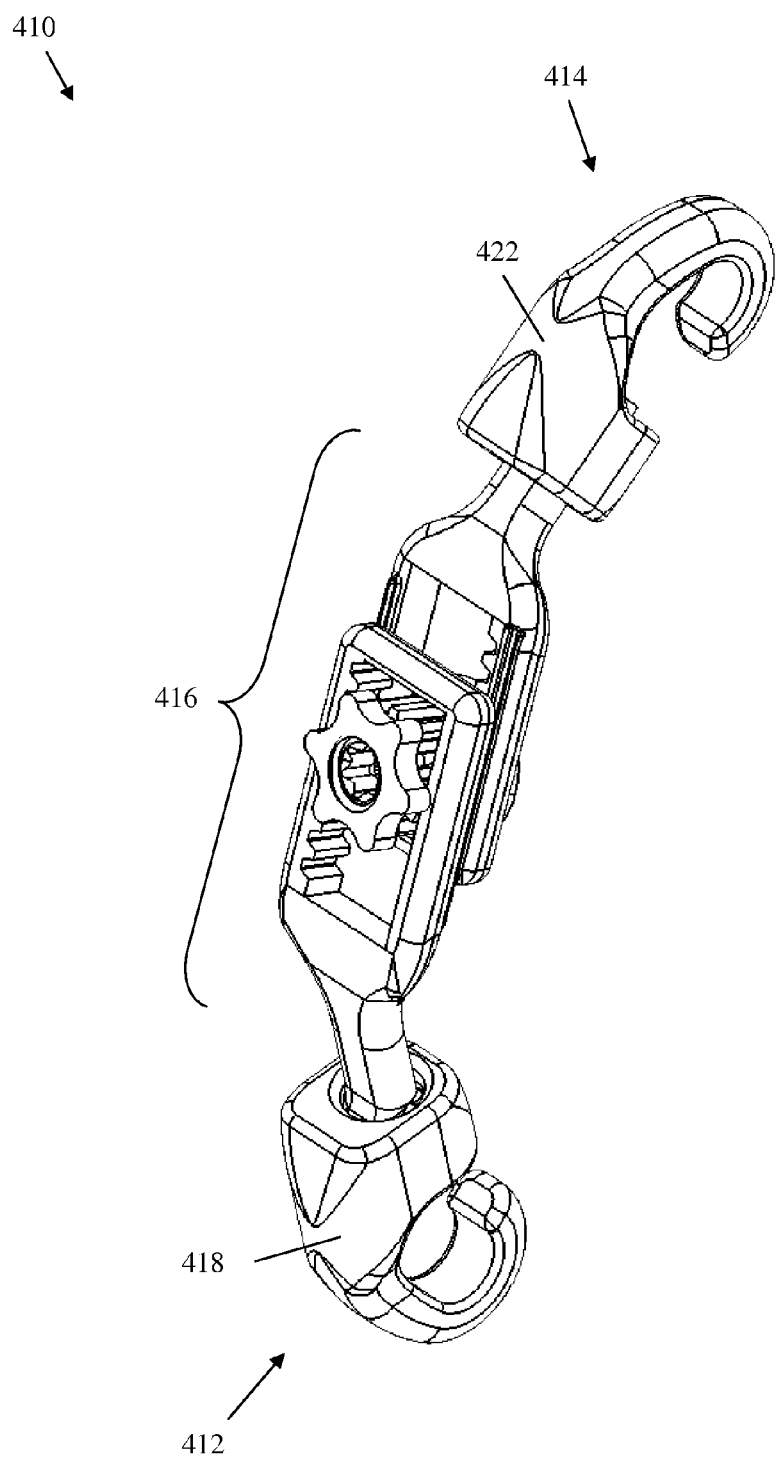
FIG. 54 is a side perspective view of an example of a cross-connector according to a third embodiment of the present invention.

FIG. 54 illustrates an example of a cross-connector 410, according to a third embodiment of the present invention. The cross-connector 410 functions the same way as cross-connector 210 and includes substantially the same structure as the cross-connector 210. Each of the parts in cross-connector 410 is identical in structure and function as the corresponding parts in cross-connector 210. Structurally, however, the cross-connector 410 has a different first coupler 418 and second coupler 422 in the first coupling assembly 412 and the second coupling assembly 414 respectively. The first coupler 418 and second coupler 422 are hook shaped and snap directly onto a rod 12.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternative falling within the spirit and scope of the invention as described herein.

What is claimed is:

1. A cross-connector for linking a pair of bilateral spinal fixation constructs, each of the bilateral fixation constructs including at least a first bone anchor having a rod receiving body, the cross-connector comprising:
   a first coupler directly coupled to the rod receiving body of the first bone anchor of one of the bilateral fixation constructs,
   a second coupler directly coupled to the rod receiving body of the first bone anchor of the other of the bilateral fixation constructs;
   a connecting arm that connects the first coupler and the second coupler;
wherein the first coupler includes a cavity for receiving the rod receiving body therein and a protrusion extending into the cavity, the protrusion being dimensioned to be received within a recess in a side wall of the rod receiving body to couple the first coupler to the rod receiving body; and wherein the first coupler includes a cam locking element that prevents decoupling of the first coupler and the rod receiving body when engaged.

2. The cross-connector of claim 1, wherein in a locked position the cam prevents the rod receiving body from moving within the cavity such that the protrusion cannot disengage from the recess in the rod receiving body.

3. The cross-connector of claim 1, wherein the first coupler is connected to the connecting arm by a joint and locking the cam also inhibits movement at the joint.

4. The cross-connector of claim 3, wherein the joint is a ball and socket joint, and wherein the socket is formed between two clamping arms of the first coupler.

5. The cross connector of claim 4, wherein the cam includes a pin having a ramped surface that rests against a ramped shelf of the first coupler such that rotating the cam lifts the cam relative to the first coupler which squeezes the clamping arms of the first coupler to inhibit movement of the ball and socket joint.

* * * * *